(12) United States Patent
Liu

(10) Patent No.: US 9,213,076 B2
(45) Date of Patent: Dec. 15, 2015

(54) SYSTEM, PROCESS AND COMPUTER-ACCESSIBLE MEDIUM FOR PROVIDING QUANTITATIVE SUSCEPTIBILITY MAPPING

(75) Inventor: Tian Liu, New York, NY (US)

(73) Assignee: MedImageMetric LLC, New York, NY (US)

(*) Notice: Subject to any disclaimer, the term of this patent is extended or adjusted under 35 U.S.C. 154(b) by 622 days.

(21) Appl. No.: 13/406,137

(22) Filed: Feb. 27, 2012

(65) Prior Publication Data

US 2013/0221961 A1   Aug. 29, 2013

(51) Int. Cl.
| | |
|---|---|
| G01R 33/565 | (2006.01) |
| A61B 5/055 | (2006.01) |
| G01R 33/24 | (2006.01) |
| A61B 5/00 | (2006.01) |

(52) U.S. Cl.
CPC ......... *G01R 33/56545* (2013.01); *A61B 5/0042* (2013.01); *A61B 5/055* (2013.01); *G01R 33/24* (2013.01); *G01R 33/56536* (2013.01)

(58) Field of Classification Search
CPC ............. G01R 33/24; G01R 33/56536; G01R 33/56545
See application file for complete search history.

(56) References Cited

U.S. PATENT DOCUMENTS

| | | | | |
|---|---|---|---|---|
| 8,422,756 B2* | 4/2013 | Haacke | ................ | G01R 33/443 250/339.07 |
| 8,693,761 B2* | 4/2014 | Haake | ................... | G01R 33/443 382/131 |
| 8,781,197 B2* | 7/2014 | Wang | ..................... | G01R 33/54 382/131 |
| 8,848,992 B2* | 9/2014 | Senegas | ........... | G01R 33/56536 324/331 |
| 8,886,283 B1* | 11/2014 | Chen | ...................... | A61B 5/055 382/128 |
| 2015/0145515 A1* | 5/2015 | Liu | ................... | G01R 33/56536 324/309 |

OTHER PUBLICATIONS

Li et al. "Quantitive susceptibility mapping of human brain refelcts spatial variation in tissue composition" Neuroimage 55, pp. 1645-1656 (2011).
Liu. "Susceptibility Tensor Imaging" Magn Reson Med 63, pp. 1471-1477 (2010).
Wu et al. "Whole brain susceptibility mapping using compressed sensing" Magn Reson Med 67, pp. 137-147 (2012).
Shmueli et al. "Magnetic susceptibility mapping of brain tissue in vivo using MRI phase data" Magn Reson Med 62, pp. 1510-1522 (2009).
Haacke et al. "Susceptibility mapping as a means to visualize veins and quantify oxygen saturation" J Magn Reson Imaging 32, pp. 663-676 (2010).

(Continued)

*Primary Examiner* — Dixomara Vargas
(74) *Attorney, Agent, or Firm* — Fish & Richardson P.C.

(57) ABSTRACT

Exemplary quantitative susceptibility mapping methods, systems and computer-accessible medium can be provided to generate images of tissue magnetism property from complex magnetic resonance imaging data using the Bayesian statistical approach. The likelihood is constructed directly using the complex data. A prior is constructed from matching structures or information content in known morphology. The quantitative susceptibility map can be determined by, e.g., maximizing the posterior. Thus, according to the exemplary embodiment, system, method and computer-accessible medium can be provided for determining information associated with at least one structure. Using such exemplary embodiment, it is possible to receive signals associated with the structure(s), where the signals can include complex data that is in the complex domain.

14 Claims, 18 Drawing Sheets

(56) References Cited

OTHER PUBLICATIONS

Liu et al. "Morphology enabled dipole inversion (MEDI) from a single-angle acquisition: comparison with COSMOS in human brain imaging" Magn Reson Med Med 66, 777-783 (2011).

Liu et al. "Calculation of susceptibility through multiple orientation sampling (COSMOS): a method for conditioning the inverse . . . " Magn Reson Med 61, pp. 196-204 (2009).

Schweser et al. "Quantitative imaging of intrinsic magnetic tissue properties using MRI single phase: an approach to in vivo brain iron . . . " Neuroimage 54, pp. 2789-2807 (2011).

Wharton at al. "Susceptibility mapping in the human brain using threshold-based k-space division" Magn Reson Med 63, pp. 1292-1304 (2010).

Wharton et al. "Whole brain susceptibility mapping at high field: a comparision of multiple- and single-oriented methods" Neuroimage 53, pp. 515-525 (2010).

de Rochefort et al. "Quantitative MR susceptibility mapping using piece-wise constant regularized inversion of the magnetic field" Magn Reson Med 60, pp. 1003-1009 (2008).

de Rochefort et al. "In vivo quantification of contrast agent concentration using the induced magnetic field for time-resolved arterial . . . " Med Phys 35, pp. 5328-5339 (2008).

Liu et al. "Unambiguous identification of superparamagnetic iron oxide particles through quantitive susceptibility mapping of . . . " Magn Reson Imaging 28, pp. 1383-1389 (2010).

Li. "Magnetic susceptibility quantification for artbitrarily shaped objects in inhomogeneous fields" Magn Reson Med 46, pp. 907-916 (2001).

Li et al. "Quantifying arbitrary magnetic susceptibility distributions with MR. Magnetic Resonance" Medicine 51:1077-1082 (2004).

Li "Averaging of harmonic physical fields over an annular region enclosing field sources" American Journal of Physics 70, pp. 1029-1033 (2002).

Li et al. "High-precision mapping of the magnetic field utilizing the harmonic function mean value property" J Magn Reson 148, pp. 442-448 (2001).

Koch et al. "Rapid calculations of susceptibility-induced magnetostatic field perturbations for in vivo magnetic resonance" Phys Med Biol 51, pp. 6381-6402 (2006).

Marques et al. "Application of a fourier-based method for rapid calculation . . . " Concepts in Magnetic Resonance Part B-Magnetic Resonance Engineering 25B, pp. 65-78 (2005).

Salomir et al. "A fast calculation method for magnetic field inhomogeneity due to . . . " Concepts in Magnetic Resonance Part B—Magnetic Resonance Engineering 19B, pp. 26-34 (2003).

Park et al. "Super-resolution image reconstruction: A technical overview" IEEE Signal Processing Magazine 20, pp. 21-36 (2003).

Farsiu et al. "Fast and robust multiframe super resolution" IEEE transactions on image processing, vol. 13, No. 10, 13, pp. 1327-1344 (2004).

Gudbjartsson et al. "The rician distribution of noisy mri data" Magn Reson Med 34, pp. 910-914 (1995).

Gindi et al. "Restoriation of a single superresolution image from several blurred, noisy, and undersampled . . . " IEEE Transactions on Medical Imaging vol. 6, 12; 1646-1658 (1997).

Gindi et al. "Bayesian reconstruction of functional images using anatomical information as priors" IEEE Transactions on Medical Imaging vol12, pp. 670-680 (1993).

Baillet et al. "A Bayesian approach to introducing anatomo-functional priors in the EEG/MEG . . . " IEEE transactions on bio-medical engineering vol. 44, No. 5, pp. 374-385 (1997).

Kressler et al. "Nonlinear regularization for per voxel estimation of magnetic susceptibility distribution from .." IEEE Transactions on Medical Imaging 29, pp. 273-28 (2010).

Liu et al. "Morphology enabled dipole inversion for quantitative susceptibility mapping using structural consistency between the . . . " Neuroimage 59, pp. 2560-2568 (2012).

Goldstein et al. "Satellite Radar Interferometry—Two-Dimensional Phase Unwrapping" Radio Science 23, pp. 713-720 (1988).

de Rochefort et al. "Quantitative susceptibility map reconstruction from MR phase data using bayesian regularization: validation and . . . " Magn Reson Med 63, pp. 194-206 (2010).

Kessler et al. "Nonlinear regularization for per voxel estimation of magnetic susceptibility distributions from MRI field maps" IEEE Trans Med Imaging 29, 273-281(2010).

Rudin et al. "Nonlinear Total Variation Based Noise Removal Algorithms" Physica D 60, pp. 259-268 (1992).

Liu et al. "A novel background field removal method for MRI using projection onto dipole fields (PDF)" NMR Biomed 24, pp. 1129-1136 (2010).

S. Smith "Fast robust automated brain extraction" Hum Brain Mapp 17, pp. 143-155 (2002).

Zubal et al. "Computerized three-dimensional segmented human anatomy" Med Phys 21, pp. 299-302 (1994).

Morgenstern et al. "Guidelines for the management of spontaneous intracerebral . . . " Stroke Journal of the American Heart Assoc. http://stroke.ahajournals.org (2013).

Flaherty et al. Long-term mortality after intracerebral hemorrhage. Neurology 66, pp. 1182-1186 (2006).

Kidwell et al. "Comparison of MRI and CT for detection of acute intracerebral hemorrhage" JAMA 292, pp. 1823-1830 (2004).

Christoforidis et al. "Size matters: hemorrhage volume as an objective measure to define significant intracranial hemorrhage associated . . . " Stroke 38, pp. 1799-1804 (2013).

Schabel, M.G. et al. "Uncertainty and bias in contrast concentration measurements using spoiled gradient echo pulse sequences" Phys Med SIOL 53, pp. 2345-2373 (2008).

Chen et al. "An optimised framework for reconstructing and processing MR phase images" Neuroimage 49, 1289-1300 (2010).

Robinson et al. "Combining phase images from multi-channel RF coils using 3D phase offset maps derived from a dual-echo scan" Magn Reson Med 65, pp. 1638-1648 (2011).

Schofield et al. "Fast phase unwrapping algorithm for interferometric applications" Optics Letters 28, pp. 1194-1196 (2003).

Reeder et al. "Iterative decomposition of water and fat with echo asymmetry and least-squares estimation (IDEAL): application with . . . " Magn Reson Med 54, pp. 636-644 (2005).

Hernando et al. "Robust water/fat separation in the presence of large field inhomogeneities using a graph cut algorithm" Magn Reson Med 63, pp. 79-90 (2010).

* cited by examiner

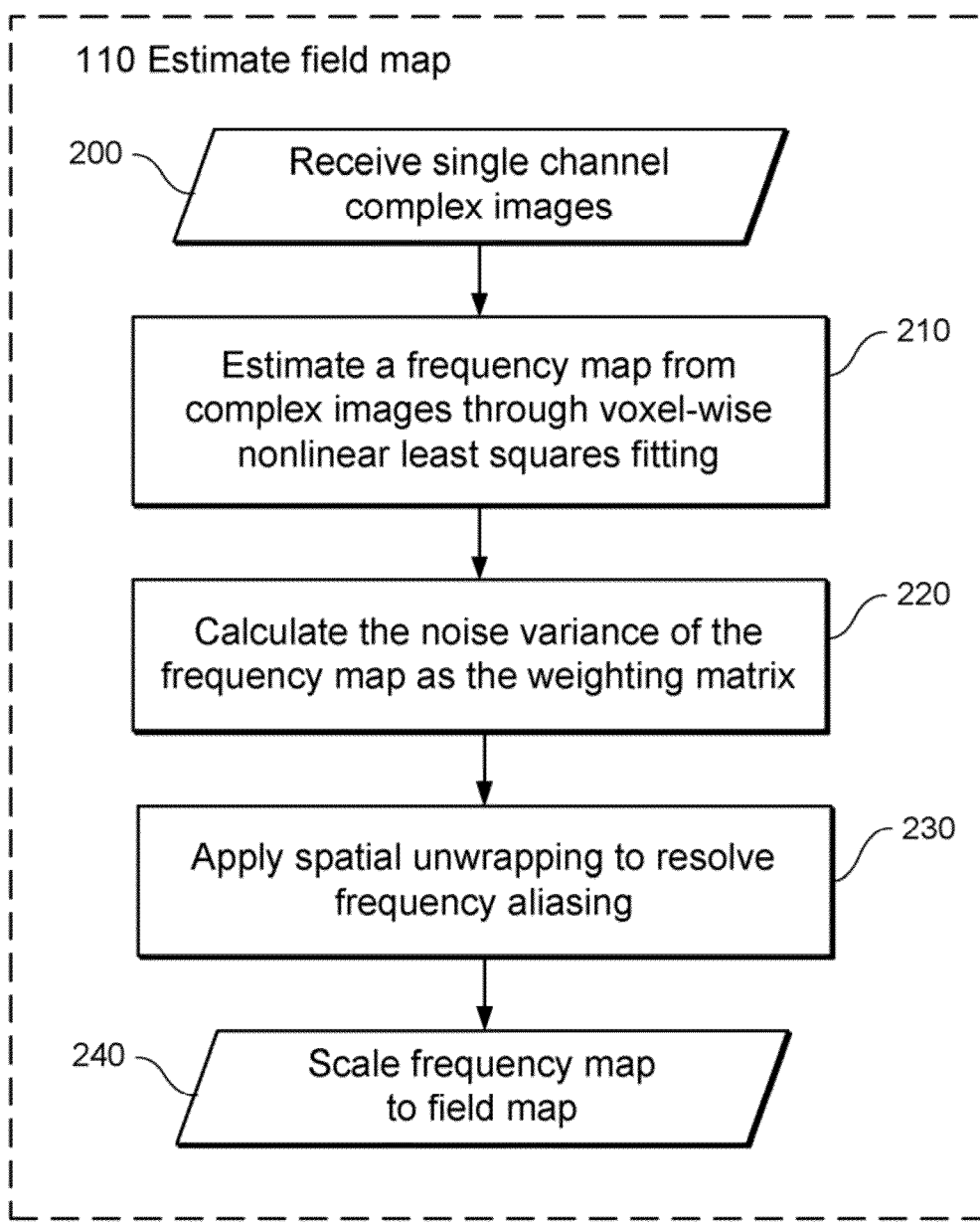
F I G. 2

FIG. 4

Matrix a (3×3):
| 0 | 0.9 | 0.9 |
|---|-----|-----|
| 0 | 0.9 | 0.9 |
| 0 | 0   | 0   |

Matrix b (3×3), with 410 pointing to center cell:
| 0.1  | 0.9 | 0.8  |
|------|-----|------|
| -0.2 | 1.0 | 0.8  |
| 0    | 0.1 | -0.1 |

Matrix c (3×3), with 420 pointing to shaded cell (1.8):
| 0.1 | 0.9 | 0.8  |
|-----|-----|------|
| 1.8 | 1.0 | 0.8  |
| 0   | 0.1 | -0.1 |

SYSTEM, PROCESS AND COMPUTER-ACCESSIBLE MEDIUM FOR PROVIDING QUANTITATIVE SUSCEPTIBILITY MAPPING

STATEMENT REGARDING FEDERALLY SPONSORED RESEARCH AND DEVELOPMENT

This disclosure was made with government support under Grant No. R43NS076092 awarded by the National Institutes of Health. The government may have certain rights in the present disclosure. This statement is included solely to comply with 37 C.P.R. §401.14(f)(4) and should not be taken as an assertion or admission that the application discloses and/or claims only a particular invention.

FIELD OF THE DISCLOSURE

The field of the present disclosure is generally related to systems, processes and computer-accessible medium which provide quantitatively susceptibility mapping, and more particular to exemplary embodiments of systems, processes and computer-accessible medium which take into consideration mapping material intrinsic physical properties as exemplified by magnetic susceptibility from signals collected in magnetic resonance imaging ("MRI").

BACKGROUND INFORMATION

Magnetic susceptibility is a physical property intrinsic to a material and measures the amount of magnetization induced in that material when placed in an external magnetic field such as the main magnetic field, $B_0$, of an MRI scanner. Using magnetic resonance imaging (MRI) to obtain a quantitative map of susceptibility provides a non-invasive means to measure the myelin in white matter tracts (see Li et al. Neuroimage 2011; 55, pp. 1645-1656; Liu. Magn Reson Med 2010; 63, pp. 1471-1477; Wu et al. Magn Reson Med 2012; 67, pp. 137-147), cortical gray matter (see Shmueli et al. Magn Reson Med 2009; 62, pp. 1510-1522), iron in deoxygenated or degraded blood and non-haem iron deposition (see Haacke et al. J Magn Reson Imaging 2010; 32, pp, 663-676; Liu et al. Magn Reson Med 2011; 66, pp, 777-783; Liu et al. Magn Reson Med 2009; 61, pp. 196-204; Schweser et al. Neuroimage 2011; 54, pp. 2789-2807; Wharton et al. Magn Reson Med 2010; 63, pp. 1292-1304; Wharton and Bowtell. Neuroimage 2010; 53, pp. 515-525), and the biodistribution of contrast agents for clinical and preclinical investigations (see Liu. Magn Reson Med 2010; 63, pp. 1471-1477; de Rochefort et al. Magn Reson Med 2008; 60, pp. 1003-1009; de Rochefort et al. lvled Phys 2008; 35, pp. 5328-5339; Liu et al. Magn Reson Imaging 2010; 28, pp. 1383-1389). Because of this promising potential, quantitative susceptibility mapping (QSM) has received increasing scientific and clinical attentions.

MRI Signal Model for Tissue Magnetic Susceptibility

The magnetic field controlling spin precession procedure can determine the MRI signal phase, allowing estimation of tissue local magnetic field (see Li. Magn Reson Med 2001; 46, pp, 907-916; Li and Leigh, Magnetic Resonance in Medicine 2004; 51, pp. 1077-1082; Li. American Journal of Physics 2002; 70, pp. 1029-1033; Li and Leigh. J Magn Reson 2001; 148, pp. 442-448). Tissue local magnetic field $b_L$ relative to, scaled to and along the main magnetic field $B_0$ in image space (referred to as r-space) can be modeled as the convolution of the dipole kernel $d(r)=(1/4\pi)(3\cos^2\theta-1)/|r|^3$ with tissue volumetric susceptibility distribution $\chi(r)$ plus observation noise $n(r)$:

$$b_L(r)=d(r)\otimes\chi(r)+n(r). \qquad [0.1]$$

This signal model for tissue magnetic susceptibility can also be expressed in the Fourier dual k-space in matrix form:

$$B_L(k)=D(k)X(k)+N(k) \qquad [0.2]$$

where $B_L=Fb_L$ with F the Fourier transform operator, $X=F\chi$, and diagonal matrix $D=Fd=1/3-k_z^2/k^2$, and $N=Fn$ (see Koch et al. Phys Med Biol 2006; 51, pp. 6381-6402; Marques and Bowtell. Concepts in Magnetic Resonance Part B-Magnetic Resonance Engineering 2005; 25B, pp. 65-78; Salomir et al. Concepts in Magnetic Resonance Part B-Magnetic Resonance Engineering 2003; 19B, pp. 26-34).

The dipole kernel can have a non-trivial null space where $D=0$, which consists of a pair of opposing cone surfaces at the magic angle)(54.7°) with respect to the $B0$ direction. This null space can make the dipole kernel undersample or subsample the susceptibility, in addition to that the dipole kernel intertwines the susceptibility. Therefore, the inverse problem of quantitatively determining the susceptibility map (QSM) from the local field is fundamentally ill-posed, and can require additional information to uniquely determine the susceptibility. The mathematical nature of QSM, as expressed in Eq. 0.1 or Eq. 0.2, can be identical to that in super-resolution image reconstruction where input image data are subsampled, warped and blurred, and noisy (see Park et al. IEEE Signal Processing Magazine 2003; 20, pp. 16; Farsiu et al. IEEE transactions on image processing: a publication of the IEEE Signal Processing Society 2004; 13, pp. 1327-1344). Regularization methods using prior information, particularly these from the Bayesian stochastic approach, can be used to derive a unique estimate of the susceptibility. However, rigorous justification and evaluation are necessary to validate any regularization method.

The noise in the local field estimated from the MRI measured signal phase in general has a complex probability distribution that can be approximated as Gaussian only when there is MRI signal-to-noise ratio (SNR)≲1 (see Gudbjartsson and Patz. Magn Reson Med 1995; 34, pp. 910-914). The Gaussian approximation is typically used in literature because of its simplicity in formulation. However, the Gaussian approximation is not valid when SNR is poor at locations with strong susceptibilities. The phase noise variance in the Gaussian approximation is the square of the inverse of SNR and can vary in space in MRI. When using the Bayesian approach to formulate the data fidelity term, this spatially varying noise variance may need to be accounted for.

Previous Methods for Quantitative Susceptibility Mapping (QSM)

The mathematical nature for the inverse problem of determining susceptibility map from field measurement is a classical super-resolution (SR) image reconstruction problem (see Park et al. IEEE Signal Processing Magazine 2003; 20, pp. 16). Known SR methods can be employed for QSM reconstruction problem, including the Bayesian statistical approach by maximizing a posteriori, i.e., maximizing the posterior distribution (see Park et al. IEEE Signal Processing Magazine 2003; 20, pp. 16; Elad and Feuer. IEEE transactions on image processing: a publication of the IEEE Signal Processing Society 1997; 6, pp. 1646-1658) that readily gives a general solution for the susceptibility by minimizing a cost function consisting of a data fidelity term $L[\chi(r)]$ associated with the likelihood function and a regularization term $R[\chi(r)]$ associated with the prior distribution:

$$\chi(r)=\mathrm{argmin}_{\chi(r)}L[\chi(r)]+\alpha R[\chi(r)], \quad [0.3]$$

where $L[\chi(r)]=\Sigma_r |w(r)[b_L(r)-d(r)\otimes\chi(r)]|^2$ with w=SNR to account for the spatial variation of noise variance in the Gaussian approximation of MRI signal phase; the regularization term is usually expressed as the $p^{th}$ power of the $L_p$ norm of a penalty function C that exponentially favors a solution of the desired property $R[\chi(r)]=\|C[\chi(r)]\|_p^p$. The anatomic prior information can be incorporated into the regularization term as a mask (see Gindi et al, Ieee Transactions on Medical Imaging 1993; 12, pp. 670-680) or weighting gradient (see Elad and Feuer. IEEE transactions on image processing: a publication of the IEEE Signal Processing Society 1997; 6, pp. 1646-1658; Baillet and Garnero. IEEE transactions on bio-medical engineering 1997; 44, pp. 374-385). Previous QSM work has contributed to the formulation of the regularization term R. Various regularizations have been tried, including the L1 norm and the square of the L2 norm of the gradient function (G) (see Kressler et al. Ieee Transactions on Medical Imaging 2010; 29, pp. 273-281), and the L1 norm of a wavelet-decomposition (see Wu et al. Magn Reson Med 2012; 67, pp. 137-147). One exemplary procedure can be the morphology enabled dipole inversion (MEDI) procedure (see Liu et al. Neuroimage 2012; 59, pp. 2560-2568) that includes an edge mask M from the gradient of anatomical prior a(r) such as the magnitude image in the regularization term, $M(r)=1$ for $|Ga(r)|<$ threshold, $M=0$ otherwise, After vectorization, the MEDI regularization term is $$R=\|MG\chi\|_1. \quad [0.4]$$

There are also non-Bayesian methods, including the truncated k-space division (TKD) method in which a threshold value can be used as the dipole kernel when its absolute value is less than the threshold (see Shmueli et al. Magn Reson Med 2009; 62, pp. 1510-1522) and the weighted k-space derivative (WKD) method in which a linear interpolation of the dipole kernel is used when its absolute value is less than a threshold (see Li et al. Neuroimage 2011; 55, pp. 1645-1656). These division methods can suffer from severe noise amplifications in the region where the dipole kernel is small.

Exemplary Limitations of Previous Methods

There are certain major exemplary limitations in the previous methods that are addressed in the present disclosure. One exemplary limitation is that the anatomic prior information is formulated as a crude edge mask as in Eq. 0.4, which tends to make the reconstructed susceptibility map blocky or pixelated in the L1 norm. This can be because small details with low contrast to noise ratio (CNR) are not captured in Eq. 0.4.

Another exemplary limitation is that in regions of high susceptibility, the SNR may be very poor due to signal loss associated with large dephasing caused by susceptibility inhomogeneity. The Gaussian model for MRI signal phase can become highly erroneous, and consequently the data fidelity term in Eq. 0.3 causes severe artifacts in the reconstructed susceptibility map.

Accordingly, there is a need to address at least some of these exemplary deficiencies and/or limitations using the exemplary embodiments of the systems, process and computer-accessible medium according to exemplary embodiments of the present disclosure.

SUMMARY OF EXEMPLARY EMBODIMENTS

In accordance with exemplary embodiments of the present disclosure, there are provided methods, systems, and computer-readable mediums for MRI signal collection and processing for reconstructing maps of physical properties intrinsic to a material, as exemplified by the magnetic susceptibility map.

One object of the exemplary embodiments of the present disclosure can be to overcome the exemplary limitation in the use of anatomical prior information. These exemplary embodiments can provide exemplary regularization methods, systems and computer-accessible medium for selecting a meaningful solution for the susceptibility map that structurally matches that of known anatomic images, including means of maximizing the correlation, mutual information, or joint entropy between the susceptibility candidate $\chi(r)$ and a known anatomy.

Another object of the exemplary embodiments of the present disclosure can provide for systems and computer-accessible medium to overcome the error in the Gaussian model for noise in the measured local magnetic field found in traditional quantitative susceptibility mapping (QSM) techniques. Certain exemplary embodiments achieve this goal by, e.g., recasting the data fidelity term in the complex MRI signal domain where the noise is actually exactly Gaussian, e.g., the linear signal equation of Eq. 0.1 is reformulated as a complex signal equation, and the quadratic data fidelity term in Eq. 0.3 is replaced by a nonlinear complex term.

Another further object of the exemplary embodiments of the present disclosure can be to apply quantitative susceptibility mapping in solving clinical problems. Certain exemplary embodiments include improving visualization of brain structures for deep brain stimulation, improving assessment of lesions of multiple sclerosis, hemorrhage, and calcification and improving evaluation of contrast agent biodistribution in contrast enhanced MRI.

Exemplary embodiments of the present disclosure include systems, processes and computer-accessible mediums for determining information associated with at least one structure. These exemplary embodiments can include at least one computing arrangement. The exemplary computing arrangement can be configured to receive signals associated with the at least one structure, wherein the signals can include complex data that is in the complex domain. These exemplary embodiments can also generate a magnetic susceptibility map for the at least one structure based on actual information having the complex data, wherein at least one portion of the actual information can relate to an actual noise property of the at least one structure.

Certain exemplary embodiments can generate the magnetic susceptibility map using a Bayesian method. This exemplary method can include constructing a Gaussian likelihood using an exponential function with a phase factor associated with a local magnetic field and using an exponential function with a phase factor associated with a susceptibility convolved with a dipole kernel. The exemplary method can also include generating a prior regarding data about the at least one structure. The exemplary method can also include maximizing a posteriori determined by the likelihood and a prior.

In certain exemplary embodiments the complex data can be used to determine the local magnetic field by employing a nonlinear least squares fitting of the complex data. Certain exemplary embodiments can apply an implicit removal of a background field caused by magnetic sources outside a region of interest so as to determine the local magnetic field by utilizing a Laplace operator. In certain exemplary embodiments, the Laplace operator can be implemented by taking a difference between a Dirac delta function and a spherical mean value function. In certain exemplary embodiments, the posteriori can be maximized by iteratively linearizing a cost function associated with the posteriori.

In certain exemplary embodiments, the posteriori can be maximized iteratively with a weighting procedure in the likelihood changing with the iteration. In certain exemplary embodiments the initial weighting can be provided according to an adjusted noise variance associated with its neighbors. In certain exemplary embodiments, the prior can be formulated using a L1 norm and the information about the at least one structure that is a structural information estimated from known images of the at least one structure. In certain exemplary embodiments, the structural information can be a gradient of the image. Certain exemplary embodiments can determine the local magnetic field by employing a spatial unwrapping procedure.

Certain exemplary embodiments can fuse the susceptibility map with anatomic images for a visualization. Certain exemplary embodiments can utilize the generated susceptibility map for visualizing subthalamic nuclei, or accessing at least one of a multiple sclerosis lesion, a cancerous lesion, a calcified lesion, or hemorrhage. Certain exemplary embodiments can utilize the generated susceptibility map for quantifying a bio-distribution of contrast agents in a contrast enhanced magnetic resonance imaging.

Another exemplary embodiment can include systems, processes and computer-accessible mediums for determining information associated with at least one structure from signals of magnetic resonance imaging, which can include receiving signals associated with the at least one structure, and generating a map of a physical property for the at least one structure using information theory procedure based on data about the at least one structure.

In certain exemplary embodiments, the physical property can include a magnetic susceptibility associated with the at least one structure, and the exemplary embodiments can generate the magnetic susceptibility using a Bayesian method. An exemplary Bayesian method can include constructing a likelihood using a local magnetic field and a susceptibility convolved with a dipole kernel, generating a prior using an information theoretic metric of the at least one structure and a susceptibility map associated with the at least one structure, and/or maximizing a posteriori determined by the likelihood and prior.

Certain exemplary embodiments can determine a magnetic field from the signals associated with the at least one structure by employing a nonlinear least squares fitting procedure. Certain exemplary embodiments can cause an implicit removal of a background field caused by magnetic sources outside a region of interest so as to determine the local magnetic field by employing a Laplace operator. In certain exemplary embodiments the Laplace operator can be implemented by taking a difference between a Dirac delta function and a spherical mean value function. In certain exemplary embodiments, the likelihood can consist of a square of a weighted L2 norm of a difference between the local magnetic field and the susceptibility convolved with a dipole kernel.

In certain exemplary embodiments, the likelihood can consist of a square of a L2 norm of a difference between an exponential function with a phase factor associated with the local magnetic field and an exponential function with a phase factor associated with the susceptibility convolved with a dipole kernel. In certain exemplary embodiments, the information theoretic metric can be a joint entropy of at least two images associated with the at least one structure. In certain exemplary embodiments the information theoretic metric can be a mutual information of at least two images associated with the at least one structure.

Certain exemplary embodiments can maximize a posteriori iteratively by linearizing a cost function associated with the posterior. Certain exemplary embodiments can maximize a posteriori iteratively with a weighting procedure in the likelihood changing with the iteration. In certain exemplary embodiments the initial weighting can be provided according to an adjusted noise variance associated with its neighbors. Certain exemplary embodiments can fuse the susceptibility distribution with anatomic images for a visualization. Certain exemplary embodiments can utilize the generated susceptibility map for visualizing subthalamic nuclei, or accessing at least one of a multiple sclerosis lesion, a cancerous lesion, a calcified lesion or hemorrhage. Certain exemplary embodiments can utilize the generated susceptibility map for quantifying a bio-distribution of contrast agents in contrast enhanced magnetic resonance imaging. Certain exemplary embodiments can determine the local magnetic field by employing a spatial unwrapping procedure.

These and other objects, features and advantages of the exemplary embodiment of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which:

FIG. 2 is a flow diagram depicting exemplary operations performed by the field map estimation procedure shown in FIG. 1;

FIGS. 4a-4c are examples of a phase map for a 3×3 image, corrupted by measurement noise containing a whirlpool shown as arrow, and consequent phase unwrapping error highlighted in a gray box;

Figure 1:
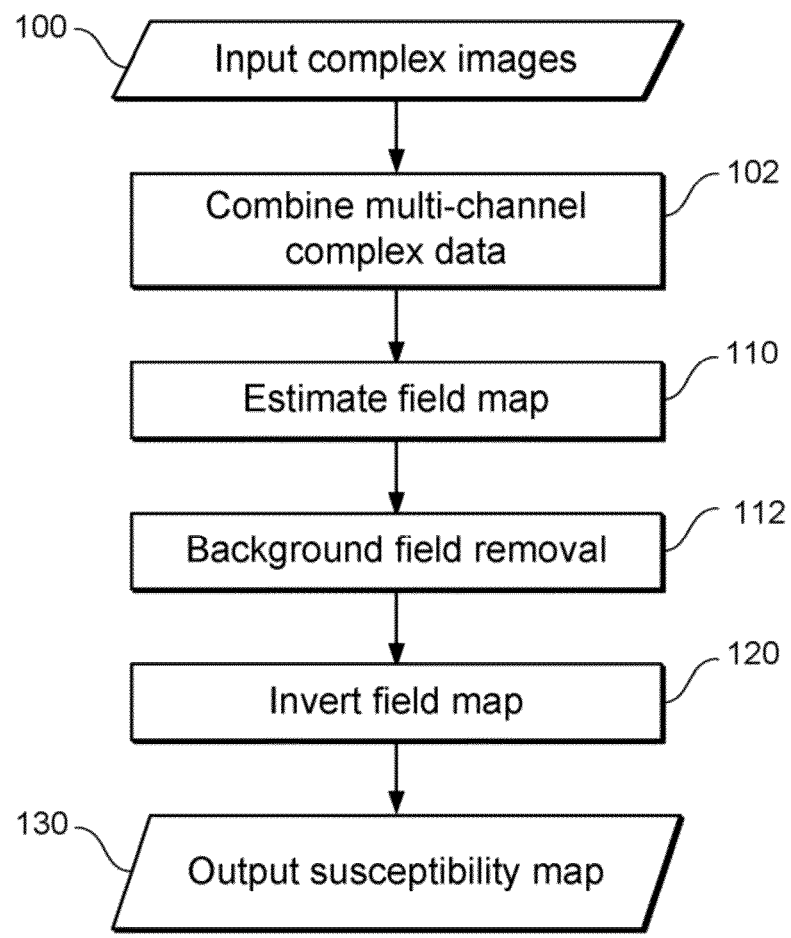
FIG. 1 is a functional block diagram of a quantitative susceptibility map generating process that can take complex volumetric MR images and outputs a volumetric susceptibility map, which can be performed by an exemplary embodiment of the system according to the present disclosure.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures or the claims appended herewith.

DETAILED DESCRIPTION OF THE EXEMPLARY EMBODIMENTS

It is to be understood that the figures and descriptions of the present exemplary embodiments have been simplified to illustrate elements that are relevant for a clear understanding of the exemplary embodiments, while removing, for purposes of clarity, other elements that are well known. The detailed description will be provided herein below with reference to the attached drawings.

Exemplary embodiments of the present disclosure can overcome deficiencies associated with various possible sources of error. To overcome certain exemplary limitations in the prior methods, it is possible to provide various exemplary arrangements to improve the regularization term and as well as other exemplary arrangement to improve the data fidelity term are proposed, respectively. Subsequently, the detailed implementation of these two exemplary methods, systems and computer-accessible medium is described, followed by experimental results illustrating the improvement.

1. Analysis of Error Sources in the MRI Signal Equation for Susceptibility Determination Sources of Errors in the MRI Phase Data In QSM, the forward problem states that the change in magnetic field $b_L$ can be defined as the convolution of a susceptibility distribution $\chi$ with the magnetic field of a unit dipole d (referred to in the following as the dipole kernel). This convolution (e.g., Eq. 0.1) can be re-expressed as a dipole kernel matrix D acting on the susceptibility distribution vector.

$$b_L = D\chi + n. \quad [1.1]$$

In MRI, the magnetic field $b_L$ can be equal to the off-resonance frequency map f scaled by the reciprocal of the gyromagnetic ratio $\gamma$. The frequency map f can be derived from noisy MR phase images involving temporal and/or spatial unwrapping. The frequency estimation may contain two sources of errors, noise and unwrapping errors, and these errors can propagate onto the calculated susceptibility distribution.

Accounting for the noise in MR phase data, the observed MR signal can be modeled as $S = A\exp(i\bar{\theta}) + \epsilon$, where A and $\bar{\theta}$ respectively denote the signal magnitude and phase in the absence of noise, $i^2 = -1$, and $\epsilon$ denotes a complex zero-mean Gaussian noise whose real and imaginary components are independent and identically distributed with a constant variance of $\sigma^2$ across the imaging volume. The phase image can be calculated pixel by pixel as the arctangent of the real and imaginary component of S. The distribution of the phase noise, $\Delta\theta = \theta - \bar{\theta}$, can have a complicated expression as given in (see Gudbjartsson and Patz. Magn Reson Med 1995; 34, pp. 910-914), which may be approximated as a zero-mean Gaussian distribution with a variance $(\sigma/A)^2 = SNR^2$ when $A \gg \sigma$, and as a uniformly distributed random variable in $(-\pi, \pi)$ when $A = 0$. However, there is no simple approximation when $A \approx \sigma$.

Phase noise may further induce unwrapping errors. In unwrapping, $2\pi$ multiples are added to or subtracted from the measured phase value in each voxel such that the differences in phase between neighboring voxels (either in time or in space) are less than π. However, noise may lead to an erroneous 2π multiple in unwrapping in one voxel, which may cascade to many downstream voxels in sequential phase unwrapping algorithms (see Goldstein et al. Radio Science 1988; 23, pp. 713-720). Additionally, noise may cause "whirlpools" in 3D phase images, where the sum of the wrapped phase differences clockwise around each set of four adjacent points is not zero. In this scenario, spatial continuity cannot to be enforced between every pair of neighboring voxels, leaving phase jumps close to 2πk with k being an integer. This problem is illustrated in FIG. 4, which illustrates numbers that are normalized by π. FIG. 4(a) illustrates true phase, FIG. 4(b) illustrates a measured noisy phase, and FIG. 4(c) illustrates an unwrapped phase. Due to the illustrated existence of a whirlpool (e.g., as illustrated by arrow 410), it may be impossible to eliminate all the discontinuities greater than π in the unwrapped phase, as exemplified in box 420.

Model Errors in Estimating f from Phase and in Dipole Convolution

The phase of a voxel measured in MRI is the phase of the complex signal from that voxel $\angle \Sigma_s \mu_s \exp(-i\gamma b_s TE + \phi_s)$, where $\angle$ denotes the phase of a complex number, $\Sigma_s$ is the summation over all spin isochromats in the voxel, $\mu_s$ denotes the strength of magnetization, $b_s$ is the local magnetic field (e.g., along $B_0$) experienced by a spin isochromat s and $\phi_s$ is the initial phase of the spin isochromat. This phase of signal from spin isochromats in a voxel can be different from the average phase of spin isochromats in that voxel, $\Sigma_s(\gamma b_s TE + \phi_s)/\Sigma_s 1$. The former is a good approximation of the latter when $b_s$ and $\phi_s$ are relatively uniform inside a voxel. This approximation breaks down when this condition is violated. The latter reflects the average of the magnetic field in the voxel and is the quantity of interest in Eq. 1.1 for susceptibility mapping. There can be other sources causing change in phase such as motion. These unaccounted phase effects can also contribute to model error.

2. Construction of Anatomical Priors

I. Improvement Upon the Formulation of Edge Matching Between Susceptibility Map and Prior Image The anatomic edge matching can be formulated into the regularization term using various edge function forms, including:

a. spatial smoothness expressed in the L2 norm of the gradient (G) (GL2) (Tikhonov regularization) (see de Rochefort et al. Magn Reson Med 2010; 63, pp. 194-206; Kressler et al. IEEE Trans Med Imaging 2010; 29, pp. 273-281)

$$R = \|G\chi\|_2^2 = \|\partial\chi/\partial x\|_2^2 + \|\partial\chi/\partial y\|_2^2 + \|\partial\chi/\partial z\|_2^2;$$

b. sparsity expressed in the L1 norm of the gradient (GL1) (see Kressler et al. IEEE Trans Med Imaging 2010; 29, pp. 273-281; Liu et al, Neuroimage 2012)

$$R = \|G\chi\|_1 = \|\partial\chi/\partial x\|_1 + \|\partial\chi/\partial y\|_1 + \|\partial\chi/\partial z\|_1;$$

c. Fractional order Lp $$R = \|G\chi\|_p^p = \|\partial\chi/\partial x\|_p^p + \|\partial\chi/\partial y\|_p^p + \|\partial\chi/\partial z\|_p^p,$$

where the Lp norm of a vector v is defined as $$\|v\|_p := \left(\sum_{i=1}^n |v_i|^p\right)^{1/p}$$

d. sparsity expressed in the original total variation norm (TV) (see Rudin et al. Physica D 1992; 60, pp. 259-268)

$$R = TV(\chi) = \sum_r \sqrt{\left|\frac{\partial\chi}{\partial x}(r)\right|^2 + \left|\frac{\partial\chi}{\partial y}(r)\right|^2 + \left|\frac{\partial\chi}{\partial z}(r)\right|^2};$$

e. sparsity expressed in a wavelet domain such as a Daubechies wavelet (Φ) (see Wu et al. Magn Reson Med 2012; 67, pp. 137-147)

$$R = \|\Phi\chi\|_1;$$

f. a combination of two sparsity terms such as total variation and wavelet (see Wu et al. Magn Reson Med 2012; 67, pp. 137-147)

$$\alpha R \to \alpha\|\Phi\chi\|_1 + \beta TV(\chi)$$

$$\alpha R \to \alpha\|G\chi\|_1 + \beta\|G\chi\|_1$$

Because these are general mathematical functions that may not always contain specific anatomic information encountered in a given application, these functions may need to be modified with anatomic prior information, such as the edge mask. An edge mask can be generated using the canny edge detection from any image reflecting anatomy, including the magnitude image, the phase image, T1 weighted image and T2 weighted image. The edge masks from different images can be combined into a composite edge mask using the union operation.

The wavelet transform can also be regarded as an edge operation, such as the Daubechies wavelet and the Haar wavelet. For each wavelet component, the binary mask of the anatomic prior a(r) can be generated from the corresponding wavelet transform with the prior image, in a manner parallel to introducing anatomic prior mask into the gradient, and the penalty function can be weighted with the prior mask accordingly:

$M(r)=1$ if $|\Phi a(r)|<$threshold; 0 otherwise.

$$R = \|M\Phi\chi\|_1;$$

II. Anatomic Prior Formulation Using Information Theoretic Metrics

Previous work on the use of anatomical priors explicitly derives an edge map from complex MR data, which usually involves taking the gradient of an image and identifying the strong gradients. Subsequently, among all the candidate solutions, the one whose boundaries have the sparsest discordance with the edges of the anatomical prior will be selected.

Exemplary embodiments of the present disclosure can provide a procedure to incorporate anatomical priors for QSM using information theory. Certain exemplary methods do not require explicit calculation of any edges or gradients. Instead, the final QSM solution can include one of the candidate solutions that has the highest similarity to the anatomical prior measured by information theoretic metrics:

$$\chi^* = \mathrm{argmin}_\chi IT(X,Y), \text{ subject to } L(\chi) = \mu \quad [2.1]$$

The information theoretic metric IT(X, Y) can denote either the joint entropy or the negative mutual information of the candidate solution K and the prior Y. According to certain exemplary embodiments of the present disclosure, it is possible to utilize $p_{X,Y}(x,y)$ to denote the joint probability density function between image X and Y, and $p_X(x)$ and $p_Y(y)$ to denote the marginal probability density function of image X and Y, respectively, and then the joint entropy can be defined as:

$$H(X, Y) = -\sum_x \sum_y p_{X,Y}(x, y) \log p_{X,Y}(x, y), \quad [2.2]$$

and the negative mutual information can be expressed as:

$$I(X, Y) = \sum_x p_X(x) \log p_X(x) + \sum_y p_Y(y) \log p_Y(y) - \sum_x \sum_y p_{X,Y}(x, y) \log p_{X,Y}(x, y). \quad [2.3]$$

The constraint $L(\chi)=\mu$, or equivalently, $\|W(D\chi-b_L)\|_2^2=\mu$, can ensure that the chosen susceptibility distribution fulfills data fidelity, i.e., the field generated by such a solution is virtually identical to the field measured from the MR data and the difference is only up to a noise level.

Because the knowledge of the derivatives of the regularization function is important for numerically solving the minimization problem using any gradient descend based solver, here we show that the derivatives of the joint entropy can be efficiently calculated with approximation. The same approximation can be extended to mutual information due to their similarity.

Sub-Procedure 1. Estimation of the Joint Probability Density Function

Although the joint histogram of images X and Y can be directly calculated from their intensities $\chi$ and a to serve as the joint probability density function, it may be a discontinuous function of $\chi$ and a, posing difficulties for any subsequent derivative calculation. Thus, we estimate the joint probability density function using the Parzen window method:

$$p_{X,Y}(x, y) = \frac{1}{N} \sum_{j=1}^{N} \phi\left(\frac{x-\chi_j}{\sigma_x}\right) \phi\left(\frac{y-a_j}{\sigma_y}\right), \quad [2.5]$$

where N is the number of voxels, $\phi(x/\sigma)$ denotes a Gaussian window of mean zero and standard deviation $\sigma$ taken as a design parameter.

Sub-Procedure 2. Calculation of the Function Derivatives

The derivative of the regularization function with respect to $\chi$ is equal to:

$$\frac{\partial R(\chi)}{\partial \chi} = \frac{\partial H(X, Y)}{\partial \chi} \quad [2.6]$$

There are two exemplary parallel approaches to calculate $\partial H(X,Y)/\partial \chi$, which are denoted here as A) interpolation approximation and B) single Gaussian approximation.

A. Interpolation Approximation

The kth element of the gradient vector $\partial H(X,Y)/\partial \chi$ can be computed from Eqs. [2.2 & 2.5] with numerical approximation:

$$\frac{\partial H(X, Y)}{\partial \chi^k} = -\frac{\Delta x \Delta y}{N} \sum_{i,j=1}^{B} (1 + \log p_{X,Y}(x_i, y_j)) \frac{\partial p_{X,Y}(x_i, y_j)}{\partial \chi_k} \quad [2.7]$$

$$= -\frac{\Delta x \Delta y}{N} \sum_{i,j=1}^{B} (1 + \log p_{X,Y}(x_i, y_j)) \times \phi\left(\frac{y_j - a_k}{\sigma_y}\right) \phi'\left(\frac{x_i - \chi_k}{\sigma_x}\right),$$

where B is the number of points at which the probability density function is computed, $\Delta x$ and $\Delta y$ equal to the range of X and Y divided by B, respectively, and $\phi'[(x_i-\chi_k)/\sigma_x]=\phi[(x_i-\chi_k)/\sigma_x][(x_i-\chi_k)/\sigma_x^2]$.

In certain exemplary embodiments, if all the voxel intensities in $\chi$ and a are located on B equispaced grid, the calculation of the joint entropy and the joint probability distribution function can actually be in the form of a convolution, which can be efficiently calculated using fast Fourier Transform (FFT). Therefore, the calculation of $\partial H(X,Y)/\partial \chi_k$ can be facilitated by first performing an intensity discretization of $\chi$ and a to $\hat{\chi}$ and $\hat{a}$, followed by the estimation $\partial H(X,Y)/\partial \hat{\chi}_k$, and finally an bilinear interpolation to obtain $\partial H(X,Y)/\partial \chi_k$.

B. Single Gaussian Approximation.

A single 2D Gaussian approximation can also be used to approximate the joint probability density function. Specifically, the sum of N bivariate Gaussians in Eq. 2.5 can be approximated by a single bivariate Gaussian of the same first and second moments by using:

$$\mu = \frac{1}{N} \sum_{j=1}^{N} \mu_j, \quad [2.8]$$

and $$\Sigma^* = \frac{1}{N} \sum_{j=1}^{N} (\Sigma_j + \mu_j \mu_j^T) - \mu^* \mu^{*T},$$

where $$\mu_j = \begin{bmatrix} \chi_j \\ a_j \end{bmatrix},$$

and $$\Sigma_j = \begin{bmatrix} \sigma^2 & 0 \\ 0 & \sigma^2 \end{bmatrix}.$$

The entropy of the fitted single Gaussian is then given by $$H(X,Y) = \frac{1}{2} \log((2\pi e)^2 |\Sigma^*|), \quad [2.9]$$

Therefore, to minimize the penalty function H(X,Y), according to exemplary embodiments of the present disclosure, it is possible to simply minimize $|\Sigma^*|$. With variable substitution, the variance $|\Sigma^*|$ reduces to:

$$R(\chi) = |\Sigma^*| = [\sigma^2 + E(a \cdot a) - E(a)^2][E(\chi \cdot \chi) - E(\chi)^2] - [E(\chi \cdot a) - E(\chi)E(a)]^2, \quad [2.10]$$

where E(a) denotes the mean voxel intensity in image a, and the symbol · denotes point-wise multiplication, and $$\frac{R(\chi)}{\partial \chi} = \frac{\partial |\Sigma^*|}{\partial \chi} = \{[\sigma^2 + E(a \cdot a) - E(a)^2]/N \times (2\chi - 2E(\chi)u) - \quad [2.11]$$
$$2[E(\chi \cdot a) - E(\chi)E(a)]/N \times (a - E(a)u)\},$$

where u denotes a vector whose elements are all 1.

3. Nonlinear Exemplary Procedure to Data Fidelity for Accurate Quantitative Susceptibility Mapping (QSM)

Nonlinear Frequency Map Estimation

In gradient echo MRI, the phase can evolve over echo time due to field inhomogeneity. Despite the complicated distribution of phase noise, the noise in the real and imaginary components of the measured complex MR signal is actually normally distributed or Gaussian. Therefore, the problem of estimating the off-resonance frequency f from complex MR signals measured at multiple TEs can be formulated as a nonlinear least squares fitting problem, $$f_r^*, \phi_{0r}^* = \mathrm{argmin}_{f_r, \phi_{0r}} \Sigma_j \| S_r(TE_j) - A_r(TE_j) \exp[i(f_r \times TE_j + \phi_{0r})] \|_2^2, \quad [3.1]$$

where the subscript r denotes a spatial location and the subscript j denote the jth echo. The phase of the true complex signal is modeled as $f_r \times TE + \phi_{0r}$, with f being the frequency of dephasing caused by field inhomogeneity and an initial phase $\phi_{0r}$, which may be caused by a mismatch between excitation frequency and local Larmor frequency.

Nonlinear Data Fidelity Term for Dipole Inversion

The exemplary calculation of susceptibility from the estimated magnetic field can be an ill-posed inverse problem in the sense that many candidate susceptibility solutions can generate virtually identical magnetic fields. Previously, the data fidelity constraint has been expressed as a linear least squares fitting. Certain exemplary embodiments of the present disclosure express the data fidelity constraint using complex exponential functions of the field and susceptibility, $$\chi^* = \mathrm{argmin}_\chi R(\chi), \text{ subject to } \| W(\exp(iD\chi) - \exp(ib_L)) \|_2^2 = \mu. \quad [3.2]$$

Here, W can be a diagonal weighting matrix reflecting the reliability of the estimated frequency of each voxel. $b_L$ can be estimated by removing a background field $b_B$ from b. μ can be the expected noise level. The complex exponential functions can be highly nonlinear in susceptibility and field, can correctly account for the noise in MR signal, and can be immune to erroneous $2\pi$ jumps in phase.

The derivatives of the nonlinear data fidelity function are also provided in the following section. First, the data fidelity term $L(\chi) = \| W \exp(iD\chi) - W \exp(ib_L) \|_2^2$ can be approximated as a quadratic function through Taylor expansion at a certain solution $\chi^{(n)}$ to the first order, $$L(\chi) = \| W \exp(iD\chi^{(n)})(1 + iD\chi) - W \exp(ib_L) \|_2^2. \quad [3.3]$$

With variable substitution $\underline{w} = W \exp(iD\chi^{(n)})$, $\underline{b} = W \exp(ib_L)$, the gradient $\partial L(\chi)/\partial \chi$ is $$\partial L(\chi)/\partial \chi = \mathrm{real}[(\underline{w}D)^H \underline{w}D\chi + (\underline{w}D)^H i(\underline{w} - \underline{b})] \quad [3.4]$$

4. Implementation of the Exemplary QSM Procedure

FIG. 1 shows a flow diagram illustrating an exemplary procedure of calculating susceptibility from MR phase data. First, one or more complex images can be input at 100, which can be followed by the below listed exemplary steps.

A. Combine Multi-Channel Data 102

This Sub-Procedure 102 can be performed, e.g., only when multi-channel data are used. When imaging the spin distribution $\rho_j$ at the j-th echo, the signal captured by the i-th channel $s_{i,j}$ can be modulated by that channel's coil sensitivity $c_i$, where $\rho$, $s_{i,j}$ and $c_i$ consist of complex numbers. When the coil sensitivities are known, the spin distribution can be estimated as $\rho_j(r) = (c^H c)^{-1} c^H s_j$, where c and $s_j$ are vectors concatenated from all the channels $c_i(r)$ and $s_{i,j}(r)$, respectively. In the case where the coil sensitivity $c_i$ is unknown, the complex image of $s_{i,k}$ from the k-th echo can serve as the coil sensitivity map. This approach can lead to a $\rho_k$ with constant zero phase, but may not change the rate of phase evolution in $\rho_1, \rho_2, \ldots, \rho_n$, which can include the quantity of interest to be estimated in the next section.

B. Field Map Estimation 110

This Sub-Procedure 110 can be performed when multi-echo data are used. Otherwise the field map can be assumed to be linearly proportional to the phase image scaled by the reciprocal of the echo time. FIG. 2 illustrates one exemplary sub-procedure, including exemplary steps for performing exemplary step 110.

For example, at 200, the exemplary procedure can receive single channel complex images. The nonlinear estimation of f and $\theta_0$ at 210 can be achieved in an iterative manner. For example, the procedure can let the field and the initial phase at the nth iteration be $f_n$ and $\phi_{0n}$, respectively (the subscript r for space can be dropped for notation simplicity), Eq. 3.1 can then be rewritten:

$$\Sigma_j |S(TE_j) - A(TE_j) \exp[i((f_n + f - f_n) \times TE_j + (\phi_{0n} + \phi_0 - \phi_{0n}))]|^2, \text{ or}$$

$$\Sigma_j |S(TE_j) - A(TE_j) \exp[i(f_n \times TE_j + \phi_{0n})] \exp[i(df_n \times TE_j + d\phi_{0n})]|^2,$$

where $df_n = f - f_n$ and $d\phi_{0n} = \phi_0 - \phi_{0n}$ are the two updates that can be estimated in order to minimize the above equation. Small updates can be used and the above equation can be linearized using Taylor expansion to the first order:

$$\Sigma_j |S(TE_j) - A(TE_j) \exp[i(f_n \times TE_j + \phi_{0n})] - A(TE_j) \exp[i(f_n \times TE_j + \phi_{0n})] i (df_n \times TE_j + d\phi_{0n})|^2,$$

leading to a quadratic function of $df_n$ and $d\phi_{0n}$ that can be solved efficiently using linear least squares fitting.

Since the true signal magnitude A may be unknown, the magnitude of s 1.5 can be used to approximate A. One exemplary initial guess of $f_0$ and $\phi_{00}$ can be estimated from the first 2 echoes through a linear fitting, where the phase at TE=0 was treated as $\phi_{00}$. The iteration can be stopped when the norm of $[df_n, d\phi_{0n}]^T$ is smaller than $10^{-4}$ times the norm of $[f_0 \ \phi_{00}]^T$ or when, e.g., n>10. The noise covariance matrix of $[df_n, d\phi_{0n}]$ can also be calculated in the approximated linear least squares fitting, and the inverse of the square root of the variance of $df_n$ constituted the weights in the weighting matrix W, e.g., at 220. The weights for voxels outside the region of interest (ROI) can be set to zero. The remaining non-zero weights can be further normalized by their average.

To address any frequency aliasing on the frequency map, two independent approaches can be applied for the spatial unwrapping (e.g., at 230). In one exemplary embodiment, a quality map guided spatial unwrapping algorithm can be applied in which the unwrapping path can be determined by the estimated noise level on the frequency map and spatial connectivity, such that less noisy regions were unwrapped first. In this method, a region growing approach can be employed starting at the center of mass of the predefined ROI. All the boundary voxel of the unwrapped region would be considered for expansion and the one with the lowest noise level would be unwrapped. This exemplary process can be repeated until all the voxels in the ROI are visited. The noise level of all the boundary voxels can be stored in a heap data structure for fast identification of the least noisy voxel.

In another exemplary approach, a Laplacian based method can be applied. This method can first calculate the Laplacian of the unwrapped frequency map using:

$$\nabla^2 \phi_{un} = \cos\phi_{un}\nabla^2\sin\phi_{un} - \sin\phi_{un}\nabla^2\cos\phi_{un} = \cos\phi_w\nabla^2\sin\phi_w - \sin\phi_w\nabla^2\cos\phi_w, \quad [4.1]$$

where $\phi_{un}$ denotes unwrapped frequency map and $\phi_w$, denotes the wrapped frequency map, and then followed by an inverse Laplace operator on $\nabla^2\phi_{un}$ to restore the frequency map $\phi_{un}$.

Finally, the unwrapped frequency map can be scaled to the relative difference field map by dividing the central frequency, e.g., at 240.

C. Dipole Inversion

Figure 3:
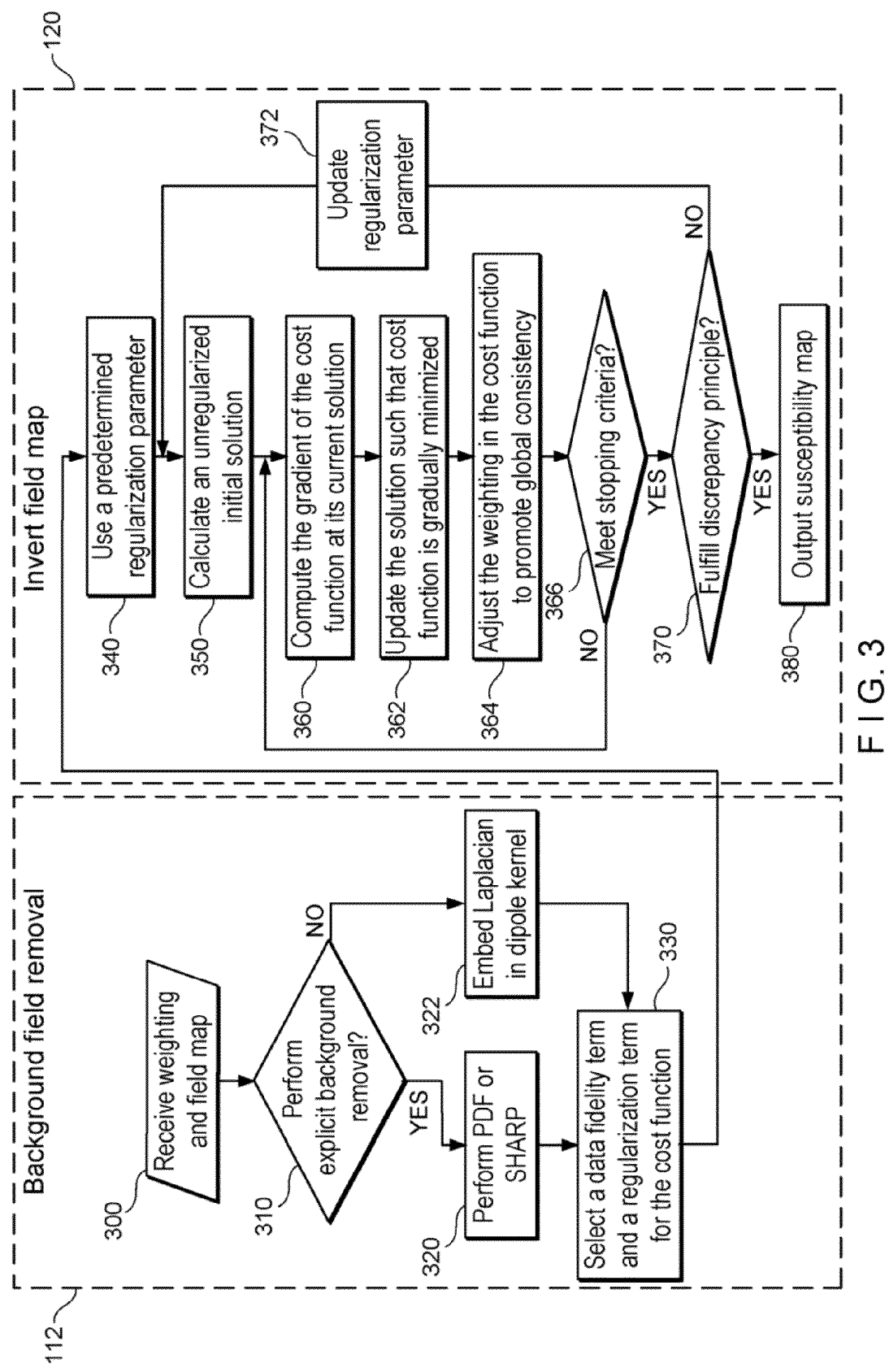
FIG. 3 is a flow diagram depicting exemplary operations performed by the field map inversion procedure shown in FIG. 1.

FIG. 3 illustrates two exemplary independent approaches that can be applied to eliminate unwanted background field contribution when calculating local susceptibility distribution, e.g., starting at Sub-Procedures 300 and 310, including a) performing an explicit background field removal, b) implicitly embedding background removal in the dipole kernel.

For explicit background field removal, either a projection onto dipole fields (PDF) algorithm (see Liu et al. NMR Biomed 2011; 24, pp. 1129-1136) or a sophisticated harmonic artifact reduction for phase data (SHARP) algorithm can be applied at 320. PDF can separate on the local field generated by magnetic sources inside a ROI from the background field. In human brain imaging, for example, the region of interest can be the brain parenchyma and was extracted automatically by a brain extraction algorithm (see Smith. Hum Brain Mapp 2002; 17, pp, 143-155). In PDF, all the voxels inside the field of view but outside the brain region can be assumed to be responsible for the background field inside the brain, and the strength of the dipole in each background voxel can be determined through a weighted least squares fit to the field inside the brain. The corrected field served as the input for the field-to-source inverse problem. SHARP exploits the fact that the background field is a harmonic function inside the brain, so it first convolves the total field b, which is the sum of background and local fields, with a Laplace operator to remove the background field contribution. After resetting the boundary condition of the ROI to zero, an inverse Laplace operator can be applied to restore the modified local field.

For implicit background field removal at 322, the field map b, the dipole kernel d, and the data weighting W can all be modified. First, a Laplace operator can be applied on b to obtain a field without any background contribution $$b_L = \nabla^2 b, \quad [4.2]$$

$\nabla^2 b$ may be further written as $$b_L = \nabla^2 b = \cos b \cdot \nabla^2(\sin b) - \sin b \cdot \nabla^2(\cos b). \quad [4.3]$$

The benefit of this approach may include that the trigonometric functions applied on b are immune to phase wrapping, preventing error propagation from insufficient phase unwrapping.

To keep consistency in the data fidelity term, the same convolution may also need to be applied to the field generated by any candidate solution: $\nabla^2 d \otimes \chi$. Certain exemplary embodiments that denote $d' = \nabla^2 d$, $d'$ and subsequent $d' \otimes \chi$ can be efficiently calculated using FFT.

One way to implement the Laplace operation $\nabla^2 y$ in Eqs. [4.1&3] can be to write it as $(\delta(r) - s(r)) \otimes y$, where $\delta(r)$ is a Dirac delta function, $s(r)$ is equal to $1/(4/3\pi R_0^3)$ when $|r| < R_0$ and 0 otherwise and y represents a scalar field. This is effectively taking the difference between a certain voxel in y and the spherical mean value (SMV) of its surrounding voxels within a certain radius. The convolution can be efficiently calculated using FFT.

When implicit background removal is used, the data weighting W may also need to be modified accordingly due to the change of noise property on $b_L$. Since $b_L = (\delta(r) - s(r)) \otimes b$, the noise variance $\sigma_{bL}^2$ on $b_L$ is: $\sigma_{bL}^2 = (\delta(r) + s(r)) \otimes \sigma_b^2$, where $\sigma_b^2$ is the noise variance on b (or equivalently, diagonal elements of W), and $\sigma_{bL}$ constitutes the diagonal elements of W'. The modified d' and W' will replace d and W in the following text if implicit background removal is chosen.

After selecting a data fidelity term and a regularization term 330, the constrained minimization problem of Eqs. [2.1&3.2] can be reformulated into an unconstrained Lagrangian minimization problem, $$\chi^* = \mathrm{argmin}_\chi L(\chi) + \alpha R(\chi). \quad [4.4]$$

An initial Lagrangian multiplier $\alpha$ can be selected empirically at 340. In one embodiment, $\alpha = 10^{-3}$. When nonlinear regularization or data fidelity term is used, the nonlinear least squares fitting problem in Eq. 4.4 can be solved in an iterative manner with an unregularized solution as initial estimate, e.g., at 350.

In each iteration, the derivative of the cost function $Q(\chi) = L(\chi) + \alpha R(\chi)$ can be calculated at its current solution 360. This derivative, after normalization to a unit length, will determine the direction at which the solution is updated up to a linear transformation. A step size will be calculated to determine the distance to go along that direction, and usually should fulfill Armijo, Wolfe, or Goldstein conditions.

Two different methods can be used to calculate the updates of the solution 362. If the Hessian matrix of the cost function can be efficiently formed such as when $\partial Q/\partial \chi$ was a linear function of $\chi$, or when the nonlinear data fidelity term and the MEDI regularization term were used, then the direction of the update can be the inverse of the Hessian matrix applied on the derivative, and a quasi-Newton method can be applied to calculate the updates.

a. Exemplary Quasi-Newton Fixed Point Method.

while $$(\|d\chi\|_2/\|\chi^{(n)}\|_2 \geq 10^{-2}) \& (n \leq 10)$$

$$d\chi \leftarrow \mathrm{argmin}_{d\chi} \|\partial^2 Q/\partial\chi^2 d\chi - \partial Q/\partial \chi\|_2$$

$$\chi^{(n+1)} \leftarrow \chi^{(n)} + d\chi$$

$$n \leftarrow n+1$$

end while

Since $\partial Q/\partial \chi^2$ is a matrix, the $d\chi \|\partial^2 Q/\partial \chi^2 d\chi - \partial Q/\partial \chi\|_2$ operation was performed using a conjugated gradient algorithm.

If $\partial Q/\partial \chi$ was not a linear function of $\chi$ or the Hessian of the cost function cannot be efficiently formed, such as when the joint entropy with interpolation approximation was used, conjugate gradient with an Armijo line search technique was applied to calculate the updates.

b. Exemplary Conjugate Gradient with an Armijo Line Search $$n \leftarrow 0; a \leftarrow 0.05; b \leftarrow 0.6;$$

while $$\|Q(\chi^{(n)}) - Q(\chi^{(n-1)})\|_2/\|Q(\chi^{(n)})\|_2 \geq 10^{-2} \& n \leq 10$$

$$t \leftarrow 1$$

$$g^{(n)} = \frac{\partial Q}{\partial \chi}(\chi^{(n)})$$

while $$Q(\chi^{(n)} + tp^{(n)}) > Q(\chi^{(n)}) + at\mathrm{real}[(g^{(n)})^* p^{(n)}]$$

$$t \leftarrow bt$$

end while $\chi^{(n+1)} \leftarrow \chi^{(n)} t p^{(n)}$ $g^{(n+1)} \leftarrow g(\chi^{(n)})$ $r \leftarrow \|g^{(n+1)}\|_2^2 / \|g^{(n)}\|_2^2$ $p^{(n+1)} \leftarrow -g^{(n+1)} + r p^{(n)}$ $n \leftarrow n+1$ end while Exemplary step 364 can include Model Error Reduction Through Iterative Tuning (MERIT). The consistency between model and measurement can be compromised in voxels inflicted by model errors, so the weighting on these voxels should be reduced to prevent error contamination to their neighbors during the inversion process. Hence, it is possible to reduce their weightings to fulfill a global consistency between magnetic field and susceptibility solution. Specifically, an updated new weighting term $W_N$ can be used to replace W in Eq. 3.2 to disfavor those voxels.

$\chi^* = \text{argmin}_\chi R(\chi)$, subject to $\|W_N(\exp(iD\chi) - \exp(ib_L))\|_2^2 = \mu$. [4.5]

The data weighting term $W_N$ in Eqs. 2.1 & 3.2 can be tuned at the end of each iteration in certain exemplary embodiments. Specifically, the weighting W in Eq. 3.2 can be reduced dynamically based on the voxel-by-voxel residual $\rho_n = W_n |\exp(iD\chi_n) - W\exp(ib_L)|$ with the subscript n denoting the nth iteration. The standard deviation of the residual $\sigma_n$ over all voxels can be estimated. A voxel v whose residual was greater than $6\sigma_n$ can be considered to be corrupted, and its data weighting can then be re-calculated as $W_{n+1,v} = W_{n,v}/(\rho_{n,v}/\sigma_n)^t$, where the exponent t determines the attenuation of the weighting and t=2, for example, was chosen in one exemplary embodiment. This iteratively reduced data weighting $W_{n+1}$ can then be used in the next iteration.

The iteration exited at 366 when the L2 norm of the update is smaller than, e.g., 1% of the L2 norm of the current solution, or the number of iterations exceeded, e.g., 10. The residual of the exit solution can be compared with the expected noise level μ. If the residual was substantially greater than μ, the regularization parameter α can be reduced to promote data fidelity, and vice versa, e.g., at 372. This process can continue until the residual approximately matches the expected noise level within 50% μ.

5. Experiments

Experiments were performed to evaluate the effectiveness of the regularization term and nonlinear data fidelity term for certain exemplary embodiments.

Assessment of the Information Theoretic Metric Term

In one exemplary experiment, five healthy volunteers (3 male, 2 female, age 25±8) were recruited for brain MR imaging on a 3T scanner (HDx, GE Healthcare, Waukesha, Wis., USA). A unipolar multi-echo gradient echo sequence with flow compensation in the readout direction (anterior/posterior) for all echoes was used. Other imaging parameters included: TR=35 ms, 8 TEs evenly spaced between 4 ms to 32 ms, bandwidth=300 Hz/voxel, field of view=24 cm, slice thickness=1 mm, acquisition matrix=240×240×150 reconstructed to 256×256×150. A parallel imaging technique (Array Spatial Sensitivity Encoding Technique) was enabled in the acquisition with an acceleration factor of 2. Real and imaginary DICOM images were saved for post-processing. Reconstructions without regularization were compared with reconstructions with a cost function Q consisting of a linear data fidelity term, and a regularization term using the joint entropy with the single Gaussian approximation. The derivative of the linear date fidelity term is $\partial L/\partial\chi = (WD)^H[W(D\chi - b_L)]$, with $A^H$ denoting the conjugate transpose of A. Because both the data fidelity and the regularization terms are quadratic functions of χ, the minimization was solved efficiently via conjugate gradient.

Assessment of the Nonlinear Data Fidelity Term

In this section, the cost function Q consisted of a nonlinear data fidelity term and the MEDI regularization $R = \|MG\chi\|_1$, where M is a binary edge mask derived from either the magnitude image, or the local field $b_L$ by setting substantial gradients to 0 and 1 otherwise. When a weak derivate of absolute value is used, $\partial R/\partial\chi = (MG)^H \text{diag}(1/|MG\chi|)MG\chi$, with diag (y) denoting a square matrix whose diagonal elements are y and 0 everywhere else. Since both $\partial L/\partial\chi$ and $\partial R/\partial\chi$ are in the form of Aχ, the Hessian matrix of both L and R can be efficiently calculated, and a quasi-Newton fixed point method was used to calculate the updates.

In the following experiments, QSM was reconstructed using both a previously developed method referred to as linear QSM, and the proposed nonlinear QSM method. All the following retrospective human studies were approved by our institutional review board. The algorithms were implemented in C on a Linux workstation with an Intel Core i7 processor and 6 GB of memory. The reconstruction time for all human data was recorded.

A. Reduction of Phase Noise Propagation

Numerical simulations were performed to examine the effectiveness of the proposed methods for reducing error due to phase noise. For the frequency map estimation, complex MR signals were simulated at 16 different TEs evenly spaced from 6 ms to 96 ms. The signal magnitude was initially 25 arbitrary units (a.u.) at TE=0 ms, and experienced an exponential T2* decay with T2*=20 ms. The true frequency was set to 50 Hz. Random zero-mean Gaussian noise with a variance of 1 a.u. was added to the real part and imaginary part independently. Linear and nonlinear field map estimation methods were used to estimate the frequency. In the linear field map estimation method, a temporal unwrapping of the radian phase was performed on a voxel-by-voxel basis by changing absolute jumps between successive echo times that are greater than or equal to π to their 2π complements, then followed by a weight least squares fitting to estimate the frequency of a voxel. The differences between the estimated and true frequency were recorded. This experiment was repeated 1000 times to study the mean and the standard deviation of the error in the frequency estimation. A student's t-test was performed to assess if there was any bias in each estimation method.

For dipole inversion, a Zubal brain phantom (see Zubal et al. Med Phys 1994; 21, pp. 299-302) was used. Different magnitude values and susceptibility values were assigned to various brain regions as summarized in Table 1. The phase was calculated directly from the assumed susceptibility distribution using a Fourier based approach. Random zero-mean Gaussian noise with a variance of 0.01 a.u. was added to the real and imaginary part of the complex image independently. The quantitative susceptibility maps were reconstructed by the linear and the nonlinear QSM methods. Their differences with respect to the ground truth were plotted.

TABLE 1

Magnitude and susceptibility values simulated in various brain regions.

| Region | Magnitude (a.u.) | Susceptibility (ppm) |
|---|---|---|
| White matter | 1 | −0.05 |
| Venous Blood | 0.7 | 0.3 |
| Caudate nucleus | 0.6 | 0.09 |
| Putamen | 0.6 | 0.09 |
| Thalamus | 0.7 | 0.07 |
| Globus pallidus | 0.5 | 0.19 |

TABLE 1-continued

Magnitude and susceptibility values simulated in various brain regions.

| Region | Magnitude (a.u.) | Susceptibility (ppm) |
|---|---|---|
| Hemorrhage | 0 | 1 |
| Other brain regions | 1 | 1 |

B. Removal of Unwrapping Error Propagation

A patient with intracranial hemorrhage was imaged at a 3T MR scanner (Trio Tim Siemens Medical Solutions, Erlangen, Germany) using a unipolar multi-echo gradient echo sequence without flow compensation. The imaging parameters were as follows: TR=45 ms, TEs=5, 10, 15, 20 ms bandwidth=200 Hz/voxel, field of view=24 cm, slice thickness=2 mm, matrix size=256×256×64, Both the magnitude and phase DICOM images were saved for post-processing. It was noted that open-ended fringe lines existed on the phase image, posing potential difficulties for spatial unwrapping.

C. Comparison of Linear and Nonlinear QSM on Volunteers

Five healthy volunteers (3 male, 2 female, age 37±16) were recruited for brain MR imaging on a 3T scanner (HDx, GE Healthcare, Waukesha, Wis., USA). A unipolar multi-echo gradient echo sequence with flow compensation in the read-out direction (anterior/posterior) for all echoes was used. Other imaging parameters included: TR=54 ms, 8 TEs evenly spaced between 6 ms to 48 ms, bandwidth=300 Hz/voxel, field of view=24 cm, slice thickness=2 mm, acquisition matrix=416×320×60 reconstructed to 512×512×60. A parallel imaging technique (Array Spatial Sensitivity Encoding Technique) was enabled in the acquisition with an acceleration factor of 2, and a partial slice encoding with a fraction of 0.75 was used to further shorten the scan time to less than 7 minutes. Real and imaginary DICOM images were saved for post-processing. The proposed nonlinear QSM was compared with the linear QSM method.

D. Imaging of Intracranial Hemorrhages

Thirteen de-identified patient cases were analyzed with intracranial hemorrhages. These images were obtained from routine patient scans on 3T MR scanners (HDx, GE Healthcare) using the same pulse sequence as in the volunteer study. The following parameters were used in clinical practice: TR=45 ms, 8 TEs evenly spaced between 5 ms to 40 ms, bandwidth=244 Hz/voxel, field of view=24 cm, slice thickness=2 mm, matrix size=acquisition matrix=240×240× 28~54 reconstructed to 256×256×28~60. A partial slice encoding with a fraction of 0.70 was used. Total scan time was proportional to the number of slices (~10 slice/minute). Magnitude and phase DICOM images were saved for post-processing. Original linear QSM, linear QSM with MERIT, nonlinear QSM without MERIT, and the proposed nonlinear QSM were also reconstructed to understand the effect of MERIT. An experienced radiologist who was blinded to the reconstruction method was asked to review the cases reconstructed using linear and nonlinear QSM and rate the image artifacts. Since noise including salt and pepper noise or checkerboard pattern and streaking artifacts appearing as shadows in axial plane were major quality issues with QSM, images were rated based on the severity of shadowing and the severity of noise, each with the same scale: 0=none, 1=moderate, 2=severe. The sum of these two score (ranging from 0 to 4) was recorded. Average scores of the linear and new reconstructions were recorded, and a Wilcox signed-rank test was performed to assess if there was any significant difference between the scores.

Results

Assessment of the Information Theoretic Term

Figure 5:
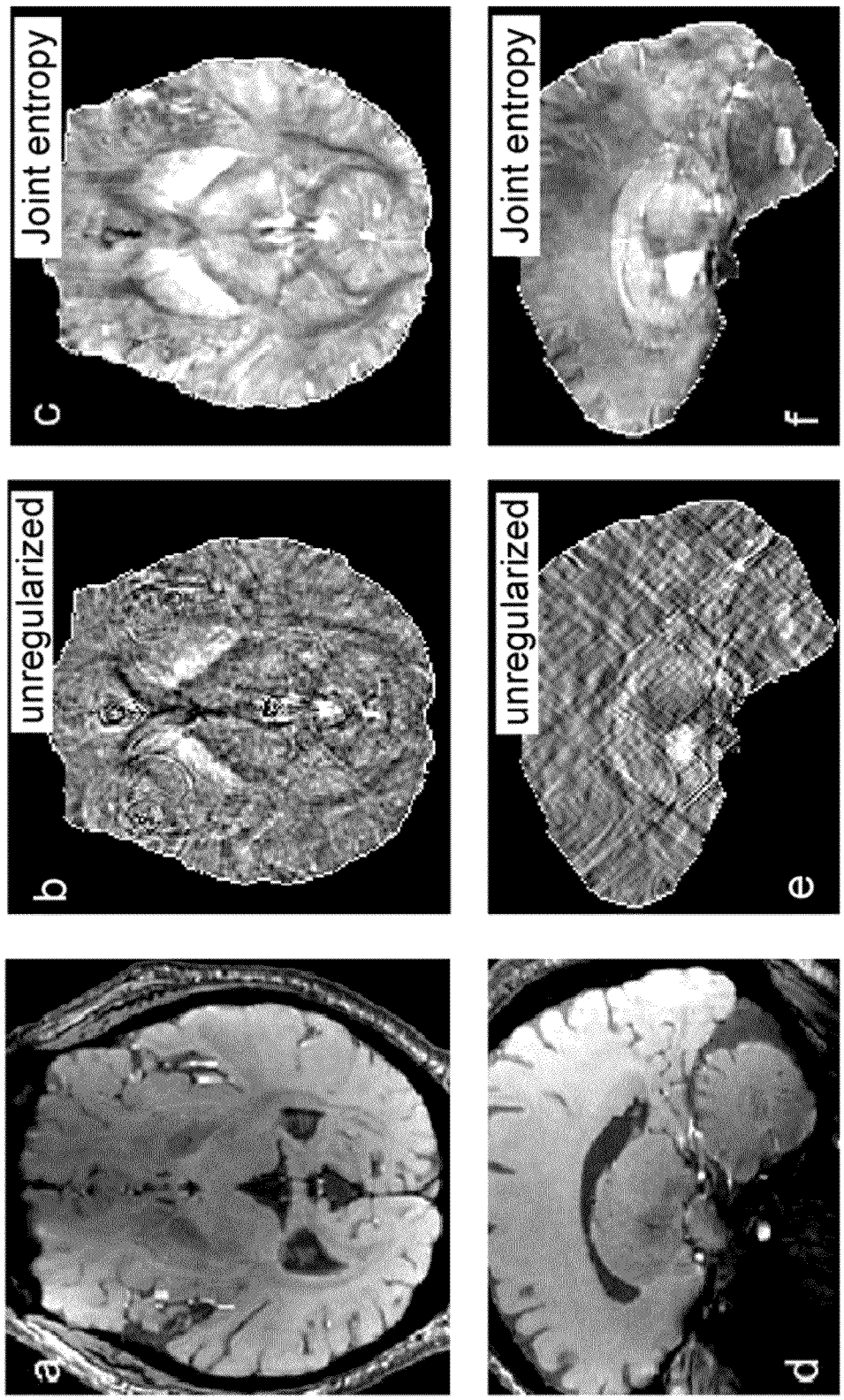
FIGS. 5a-5c are, in an axial view, examples of an anatomical prior, unregularized susceptibility solution, and the markedly improved susceptibility solution using an exemplary joint entropy regularization procedure.
FIGS. 5d-5f are, in sagittal view, images of the anatomical prior, unregularized susceptibility solution, and the markedly improved susceptibility solution using the exemplary joint entropy regularization procedure for the case in FIGS. 5a-5c.

The unregularized reconstruction, in one exemplary experiment, had severe streaking artifacts, which are pronounced on the sagittal plane. These streaking are successfully removed on the joint entropy regularized reconstruction (FIG. 5). The anatomical prior (FIGS. 5a&d), unregularized solutions (FIGS. 5b&e) and joint entropy regularized solutions (FIGS. 5c&d) are shown in axial and sagittal sections. Regularized solution successfully removed the artifacts seen in FIGS. 5b&e.

Assessment of the Nonlinear Data Fidelity Term

A. Reduction of Phase Noise Propagation

Figure 6:
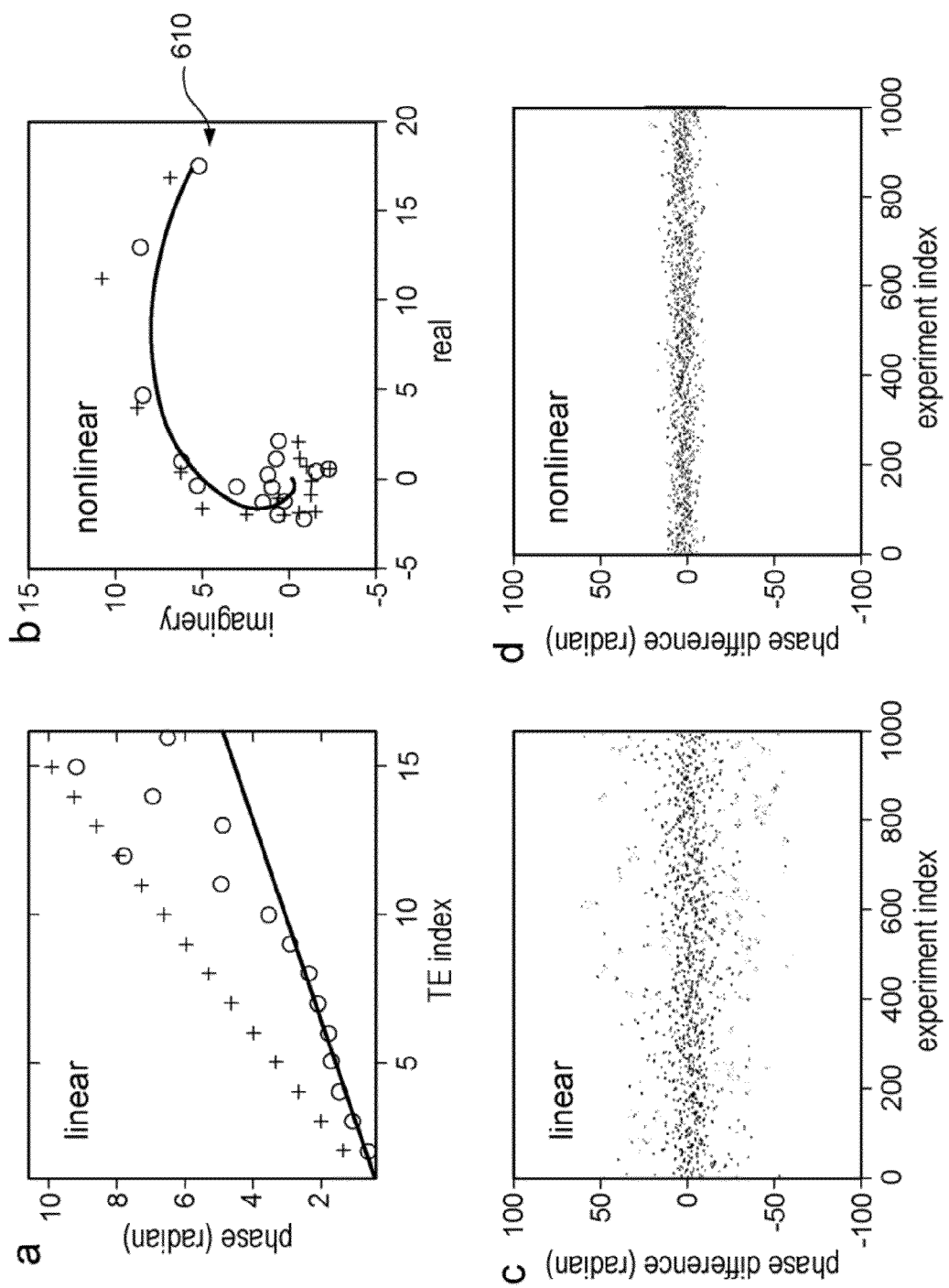
FIGS. 6a and 6b are graphs of exemplary cases where noise in the measured phase (e.g., circle) caused marked deviation of the fitted phase (e.g., cross) from the true phase (e.g., solid line) in the case of linear phase fitting, and this noise corruption problem was substantially reduced in the complex plane used in the nonlinear fitting.
FIGS. 6c and 6d are graphs, in 1,000 repeated experiments, each providing respective generated noise, the difference between estimated field and true field showed greater variation in the linear fitting method than the nonlinear fitting.

The comparison of the frequency map estimation between linear and nonlinear fitting is shown in FIG. 6. An exemplary case where the linear fitting method failed is shown in FIG. 6a, in which the noise corrupted the phase of the later echoes. The noise corruption problem was reduced in the complex plane used in the nonlinear fitting method (FIG. 6b). The rightmost point 610 on FIG. 6b corresponded to the signal measured at the first TE with the greatest signal strength. As TE progressed, the signal points converged to (0, 0) on the complex plane in a counter-clockwise motion. Neither method showed significant bias in the frequency map estimation (mean=−0.39 Hz and −0.12 Hz, P=0.44 and 0.42 for linear and nonlinear fittings, respectively) (FIGS. 6c&d). However, the standard deviation of the difference is markedly reduced in the nonlinear fitting (std=16.1 Hz and 4.8 Hz for linear and nonlinear fittings, respectively).

Figure 7:
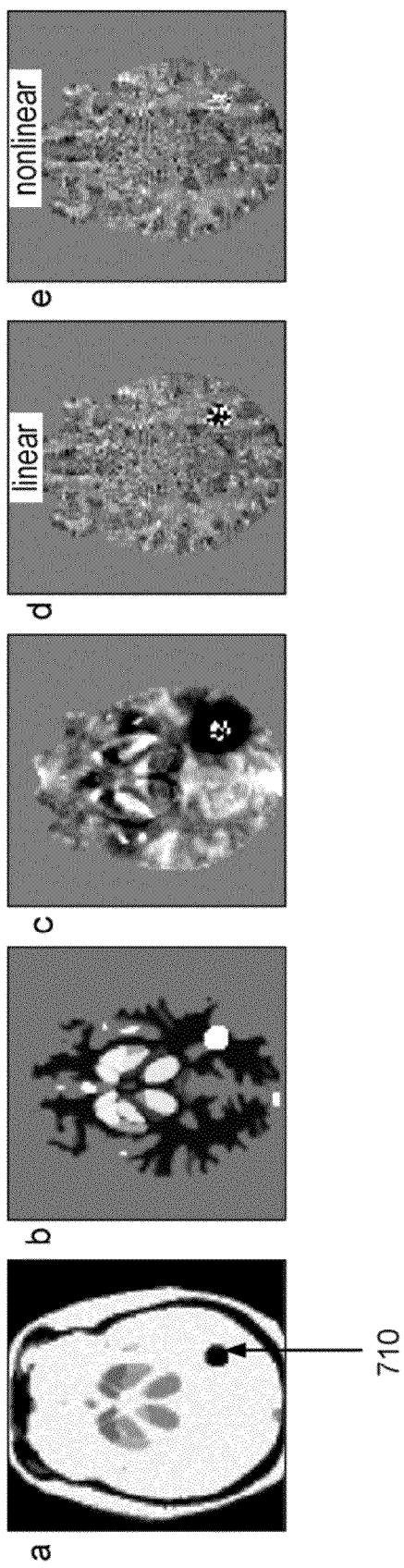
FIGS. 7a-7e are exemplary magnitude image, true susceptibility distribution, local field, difference image between linear QSM reconstruction and gold standard showing large error inside the hemorrhage, and the difference image between nonlinear QSM reconstruction and the standard with much reduced error inside the hemorrhage.

The comparison of the linear and nonlinear data fidelity term for dipole inversion is shown in a numerical phantom (FIG. 7). Due to low signal strength in the hemorrhage 710 (FIG. 7a) the field value inside the hemorrhage is corrupted by noise (FIG. 7c). When using the linear dipole inversion, the corrupted field leads to corrupted susceptibility values within the hemorrhage (FIG. 7d). The nonlinear fitting removed the severe noise in the hemorrhage (FIG. 7e), leading to higher accuracy compared to the ground truth (FIG. 7b). The root mean square error in the hemorrhage was 0.39 ppm in the linear QSM and 0.04 ppm in the nonlinear QSM, corresponding to 39% and 4% of relative error.

B. Removal of Unwrapping Error Propagation

The magnitude images directly acquired from the scanner are shown in a sagittal section (FIG. 8a) and an axial section (FIG. 8f). The open-ended fringe line on the phase image (FIGS. 8b&g) caused incomplete spatial unwrapping on the frequency map (FIGS. 8c&h), which subsequently lead to severe streaking artifact in the linear QSM (FIGS. 8d&i) because the linear data fidelity term was unable to model these abrupt discontinuities. The streaking artifacts were removed in FIGS. 8e&j using the nonlinear QSM reconstruction method. The reconstruction time was 4 minutes for both linear and nonlinear QSM reconstruction.

C. Comparison of Linear and Nonlinear QSM on Volunteers

Figure 9:
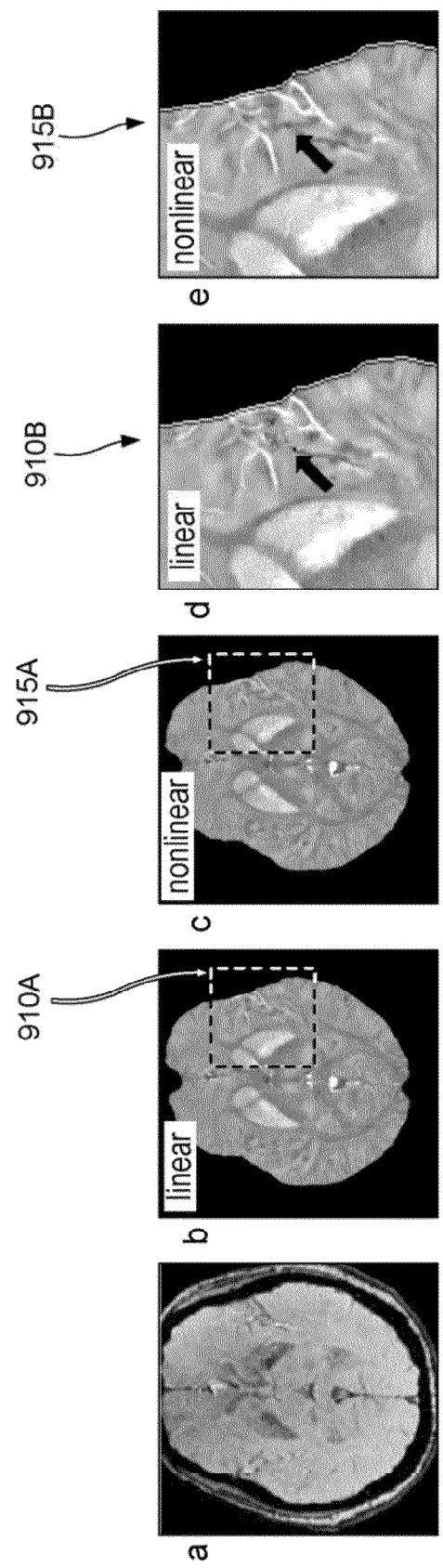
FIGS. 9a-9e are exemplary magnitude image, linear QSM, nonlinear QSM, zoomed (dashed box) linear QSM, and zoomed nonlinear QSM demonstrating subtle improvements over linear QSM as pointed by arrows.

In 3 out of 5 exemplary test cases, nonlinear QSM improved image quality in the following regions where linear QSM occasionally produced artifacts: 1) interior of vessels showing salt and pepper noise, 2) exterior of vessels showing checkerboard pattern or dark shadow, and 3) basal ganglia regions with high susceptibility showing checkerboard pattern. An example is shown in FIG. 9. The magnitude image of an example case is shown in FIG. 9a. The linear and nonlinear QSM reconstruction showed a high degree of similarity by visual inspection (FIGS. 9b&c). Zoom-in of the dashed box 910A and 915A is shown in FIGS. 9 d&e respectively, i.e., 915A and 915B. The nonlinear QSM (FIG. 9e) demonstrated subtle improvements over linear QSM (FIG. 9d) as pointed by arrows. Otherwise, the linear and nonlinear QSM showed a high degree of similarity by visual inspection. The reconstruction time was 17±2 minutes for both linear and nonlinear QSM reconstruction.

D. Imaging of Intracranial Hemorrhages

Figure 10:
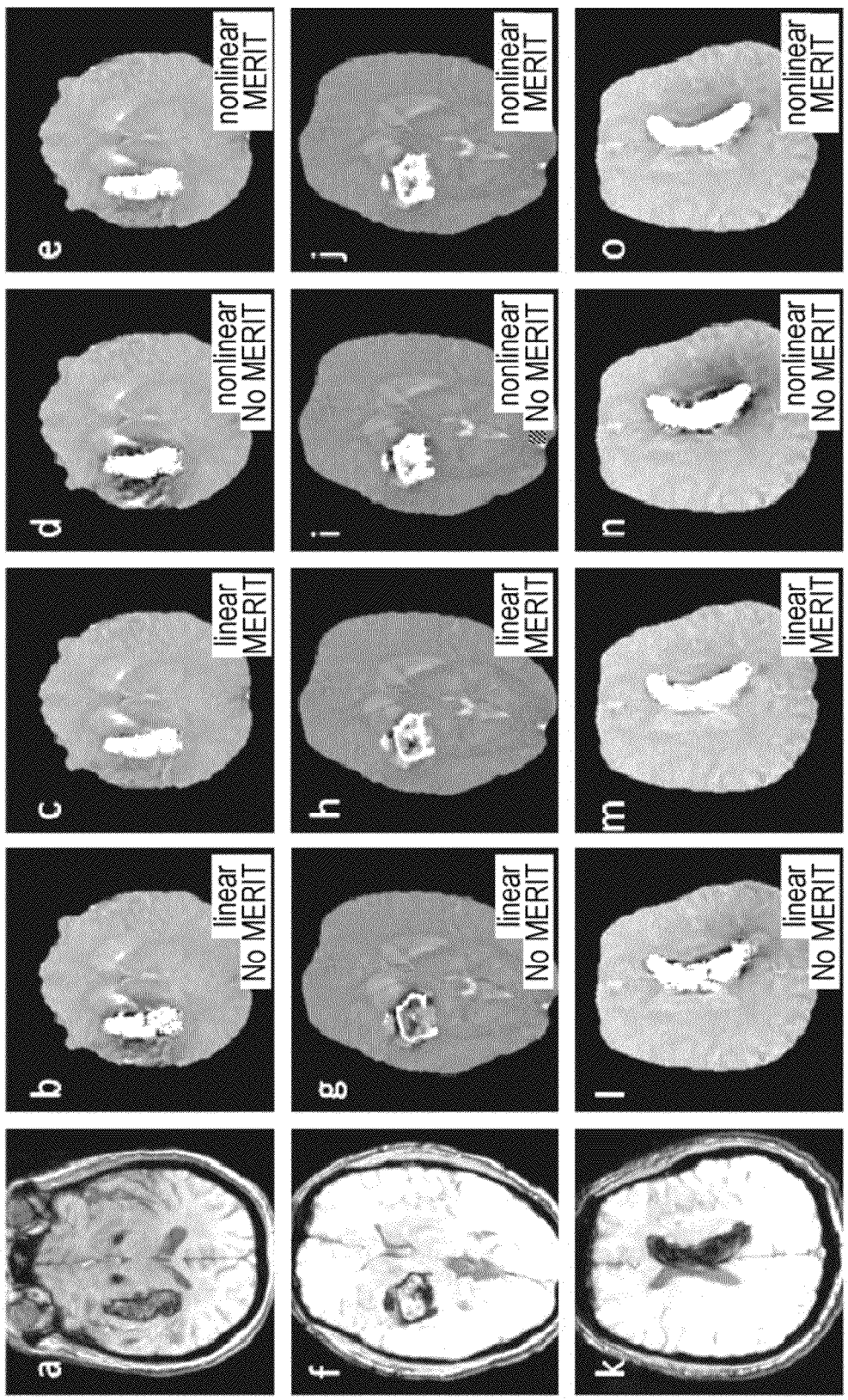
FIGS. 10a-10e illustrate an example of intracranial hemorrhage magnitude images, linear QSM showing shadowing and noisy artifacts, MERIT linear QSM showing much reduced shadowing artifacts, nonlinear QSM without MERIT showing shadowing but no noise artifacts, and MERIT nonlinear QSM showing marked reduction of both the noise and shadowing artifacts associated with the hemorrhage.
FIGS. 10f-10j are second exemplary intracranial hemorrhage magnitude images, linear QSM showing shadowing and noisy artifacts, MERIT linear QSM showing much reduced shadowing artifacts, nonlinear QSM without MERIT showing shadowing but no noise artifacts, and MERIT nonlinear QSM showing marked reduction of both the noise and shadowing artifacts associated with the hemorrhage.
FIGS. 10k-10o are third exemplary intracranial hemorrhage magnitude images, linear QSM showing shadowing and noisy artifacts, MERIT linear QSM showing much reduced shadowing artifacts, nonlinear QSM without MERIT showing shadowing but no noise artifacts, and MERIT nonlinear QSM showing marked reduction of both the noise and shadowing artifacts associated with the hemorrhage.

The magnitude image of three representation cases are shown in FIGS. 10a,f&k. In comparison, MERIT was effective in reducing the shadowing artifacts on the QSM (FIGS. 10c, h, m), and the nonlinear data fidelity term was effective in reducing the noise inside the hemorrhage (FIGS. 10d, i, n), which was in agreement with the simulation results. (FIG. 7e). By combining these two, nonlinear QSM FIGS. 10e,j&o showed significantly improved image quality (P<0.001) compared to linear QSM (FIGS. 10b, g&l). The average score of linear QSM was 2.6±1.1 (mean±standard deviation) while the scores of nonlinear QSM was 0.5±0.7. The artifacts scores in nonlinear QSM were unanimously lower than linear QSM. The reconstruction time was 3±1 minutes for both linear and nonlinear QSM reconstruction.

Further Exemplary Embodiments

In certain exemplary experiments above, robustness could be a bottleneck, preventing routine QSM practice. In certain exemplary embodiments of the present disclosure, a nonlinear QSM reconstruction method can be used, in which phase noise and unwrapping errors are properly accounted for and unexpected errors receive reduced weighting. Nonlinear QSM can show significant improvement in regions with low signal to noise ratio while keeping the reconstruction time similar to that of the linear QSM reconstruction. The enhanced image quality can be helpful for imaging intracerebral hemorrhages.

Intracerebral hemorrhage (ICH) is a devastating disease constituting 10-15% first ever strokes in US and 30% of strokes in Asia (see Broderick et al. Circulation 2007; 116, pp. e391-413) and having the highest mortality rate of all stroke subtypes with a 1-year survival rate of less than 50% (see Flaherty et al. Neurology 2006; 66, pp. 1182-1186). MRI can play an important role in both clinical practice and research development in the treatment of acute ICH, because of its rich tissue contrasts and high sensitivity to the presence of ICH (see Kidwell et al. JAMA 2004; 292, pp. 1823-1830). Traditional MRI techniques are limited to detection of ICH and are generally not quantitative. Treatment of ICH can require quantitative measurement of ICH including hematoma volume measurement (see Christoforidis et al. Stroke 2007; 38, pp. 1799-1804). The QSM method through deconvolution can remove blooming artifacts in T2* weighted magnitude images and can enable reliable quantitative hematoma volume measurement. QSM may be used to precisely measure the susceptibility changes over the age of hematoma as blood product degenerates from oxyhemoglobin (hyperacute ICH), deoxyhemoglobin(acute), methemoglobin (subacute) to hemosiderin and ferritin (chronic). Therefore, QSM may provide useful quantitative information in ICH patient management.

Another potential exemplary application of nonlinear QSM would be quantifying negative contrast agents such as SPIO, which possesses strong susceptibility and creates signal voids on gradient echo image similar to hemorrhages. Quantification of SPIO in preclinical model would be useful to monitor drug delivery in cancer therapy or inflammation. Similarly, QSM can be used to quantify Gadolinium-based positive contrast agents that have been widely used in clinical practice but are difficult to quantify in vivo using traditional T1/T2 enhancements that are susceptible to various errors including saturation, flip angle imprecision and motion effects (see de Rochefort et al. Med Phys 2008; 35, pp. 5328-5339; Schabel and Parker. Phys Med Biol 2008; 53, pp. 2345-2373). Accurate in vivo quantification can lead to accurate assessment of tracer kinetic parameters such as $k_{tr}$ that may improve diagnostic specificity such as in brain cancer diagnosis.

On the technical end, an improvement in nonlinear QSM is the better management of noise in MR data. The linear least squares fitting in MEDI leads to a statistically optimal solution only when the noise in phase is Gaussian. It is justifiable to use linear QSM in a healthy volunteer because the phase noise can be approximated as Gaussian when SNR is high. However, this assumption may not hold true in hemorrhagic lesions, such as illustrated in FIG. 4. In this scenario, the zero-mean Gaussian noise in the real and imaginary parts were correctly accounted for by the nonlinear QSM, and the susceptibility inside the hemorrhage was estimated from the surrounding magnetic fields exploiting the long-range nature of the dipole fields. Therefore, nonlinear QSM showed significant improvement in the lesion regions in terms of noise reduction.

Figure 8:
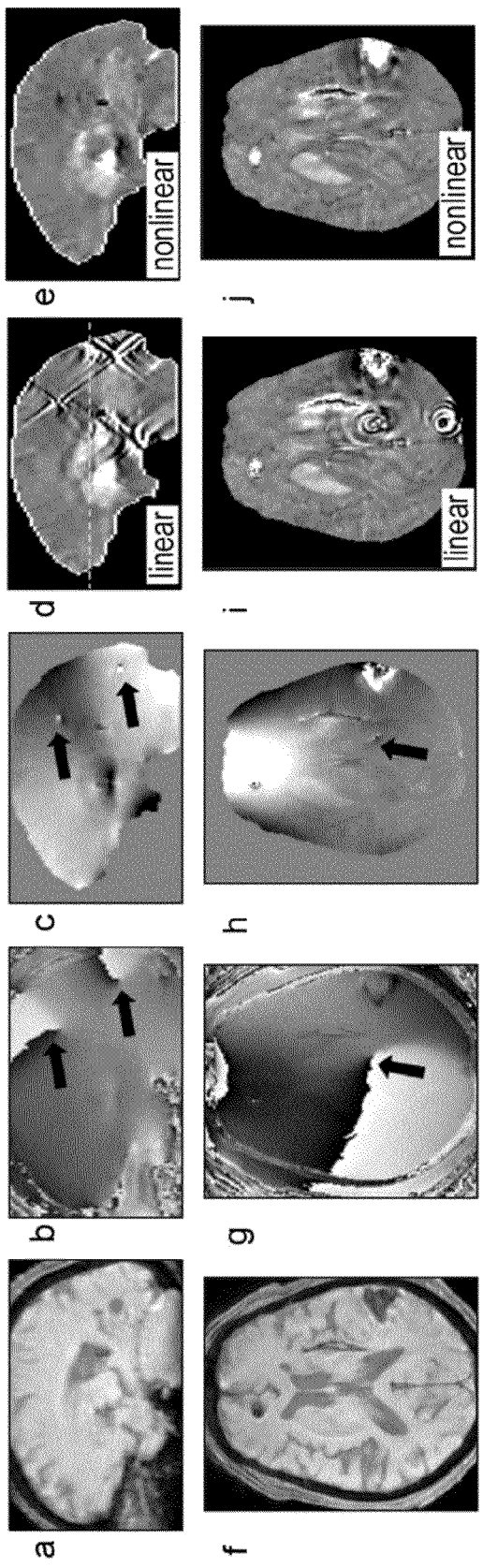
FIGS. 8a-8e are exemplary magnitude image, phase image with open-ended fringe lines (black arrows), frequency map with consequent unwrapping errors (black arrows), QSM reconstructed with the linear method showing severe streaking artifacts, and QSM reconstructed with the nonlinear method showing no streaking artifacts, in sagittal view.
FIGS. 8f-8j are exemplary images, in axial view of those shown in FIGS. 8a-8e (the axial section indicated in FIG. 8d by the white dashed line), depicting magnitude image, phase image with open-ended fringe lines (black arrows), frequency map with consequent unwrapping errors (black arrows), QSM reconstructed with the linear method showing severe streaking artifacts, and QSM reconstructed with the nonlinear method showing no streaking artifacts.

Unwrapping error can be a major problem that can prevent robust QSM reconstruction. Although numerous unwrapping algorithms have been proposed, the integration of phase unwrapping into QSM traditionally was not always reliable. Due to the long-range nature of the dipole field, even a local phase jump in the frequency map may propagate a long way, e.g., as seen in FIG. 8. In certain exemplary embodiments of the present disclosure, temporal unwrapping was completely bypassed in the nonlinear frequency map estimation, eliminating temporal unwrapping errors. There are several exemplary strategies to further reduce the spatial unwrapping error. The open-ended fringe line on the phase image (FIGS. 8b&g) may be avoided if other methods are used to combine multiple channel raw data into a single phase image (see Chen et al. Neuroimage 2010; 49, pp. 1289-1300; Robinson et al. Magn Reson Med 2011; 65, pp. 1638-4648). The spatial discontinuity in FIGS. 8c&h may be eliminated in minimum-norm based spatial unwrapping methods (see Li et al. Neuroimage 2011; 55, pp. 1645-1656; Ghiglia and Pritt. 1998; xiv, 493 p. 178-277; Schofield and Zhu. Optics Letters 2003; 28, pp. 1194-1196). However, minimum-norm based methods are qualitative because the difference between unwrapped and wrapped phase may almost never be a $2\pi$ multiple, undermining the quantitative nature of susceptibility mapping. As an attempt to completely bypass spatial unwrapping, certain exemplary embodiments also reformulate the least squares fitting problem in PDF as a nonlinear fitting in the complex plane, and apply the same iterative solver employed in the dipole inversion to nonlinear PDF. A linear PDF can be performed to obtain an initial guess of the background dipole distribution for fast convergence in the nonlinear PDF. Certain exemplary nonlinear PDF results may not show marked improvement over linear PDF in the example case shown in FIG. 8, indicating that unwrapping error may be less of a problem for background field removal than for dipole inversion. Therefore, a fully nonlinear version of the QSM procedure can be feasible according to certain exemplary embodiments and may be more robust against spatial unwrapping errors compared to linear QSM, because the phase was mapped to the complex plane and was immune to erroneous $2\pi$ jumps.

The exemplary MERIT method is similar to the iteratively reweighted least squares (IRLS) method commonly used in robust regression as a way to reducing the influence of outliers in an otherwise normally-distributed data set. IRLS can minimize the data fidelity term using the $L_p$ norm where p=2-2t (see Björck. 1996; xvii, 408p. 173-405) with t defined in the implementation section. There are differences between certain exemplary embodiments and the traditional IRLS. These certain exemplary embodiments can apply reduction of weighting to voxels selectively, while IRLS traditionally applies reweighting (decreasing or increasing weighting) to all voxels. Certain exemplary embodiments empirically found in this preliminary study that MERIT at t=2 provides effective reduction of artifacts associated with corrupted data points that cannot be modeled well. Field model error may be substantial in regions with high susceptibility (~1 ppm) that may lead to intravoxel field dispersion $\gamma \, \delta b_s \sim 1/TE \sim 50$ Hz at TE=20 ms. It may also occur at locations with motion including flow.

Although a $L_1$ norm regularization that encourages similarity to anatomical structures were used in combination with the proposed nonlinear least squares fitting, the nonlinear data fidelity term may not be not bound to this specific regularization approach and could be generally applicable to various regularization methods. The combination of nonlinear fitting with MEDI can be a good match because the $L_1$ regularization term in MEDI can already require a nonlinear solver, such additional nonlinear data fidelity term did not require an additional solver or increase calculation time. The linearization procedure outlined in the above exemplary method section can be shown to be well-behaved, leading to the same convergence behavior as the linear QSM method.

The nonlinear frequency map estimation method may be similar to the Iterative Decomposition of water and fat with Echo Asymmetry and Least-squares estimation (IDEAL) method (see Reeder et al. Magn Reson Med 2005; 54, pp. 636-644). Frequency map estimations of certain exemplary embodiments can be more robust than IDEAL, because the number of unknown variables can be less than in IDEAL and there can be more echoes available. One known problem in water-fat separation is that the solution often depends on the initial guess, and a local minimum tends to be found instead of the global minimum. This problem can be avoided in certain exemplary embodiments' nonlinear frequency map estimation by calculating the initial guess of frequency from the first two echoes that are already very close to the final solution. However, the data fidelity term in dipole inversion may still have its convergence subject to the initial guess. This problem can be addressed in certain exemplary embodiments using an initial guess closer to the final result, such as the one estimated from linear QSM, or more intelligent solvers such as graph cut based algorithms (see Hernando et al. Magn Reson Med 2010; 63, pp. 79-90).

Exemplary embodiments of the present disclosure include a nonlinear QSM reconstruction method in which phase noise and unwrapping errors are properly accounted for and reweighting can be used for more robust fitting. The phase unwrapping problem and the non-Gaussian phase noise problem can be overcome using this nonlinear approach. Numerical simulation and patient data showed significant improvement in regions with low signal to noise ratio. The enhanced image quality is especially helpful for imaging intracranial hemorrhages.

Exemplary Applications

In the following exemplary applications, the complex MR data were processed with nonlinear field map estimation, implicit background removal, and a nonlinear data fidelity term with the MEDI regularization.

Visualizing Deep Brain Nuclei and White Matter Fiber Tracts

Figure 11:
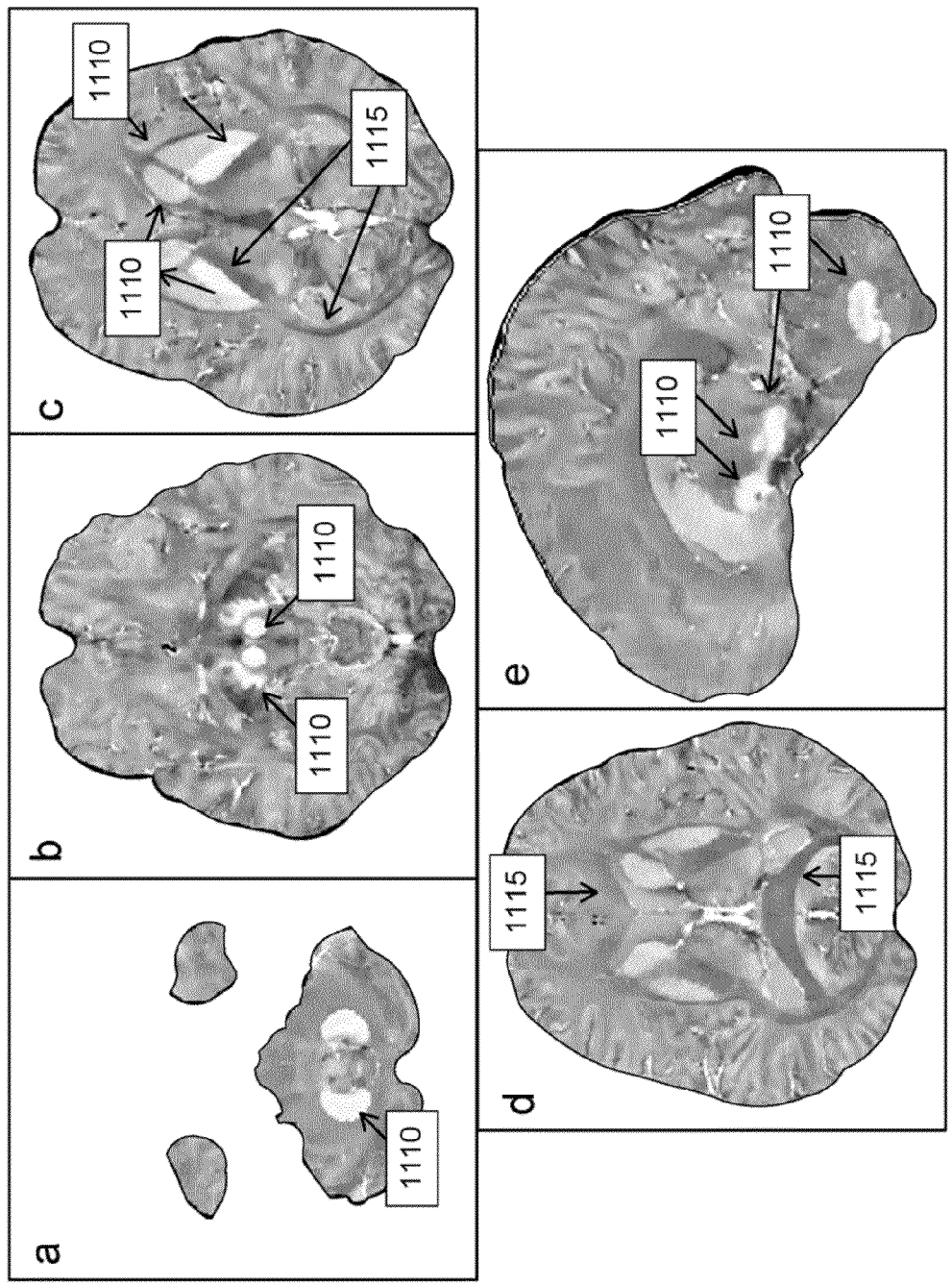
FIGS. 11a-11e are exemplary images of deep brain nuclei (black arrows) and white matter fiber tracts (white arrows) in axial and sagittal views.

Because iron possesses strong paramagnetism and deep brain nuclei often have rich iron deposition relative to surrounding tissues, quantitative susceptibility mapping can provide clear delineation of the deep brain nuclei and white matter fiber tracts, which is illustrated in FIG. 11. In this exemplary illustration, the complex MR data was acquired on a 3T scanner using a multi-echo gradient echo sequence with the following exemplary scanning parameters, flow compensated in readout direction (anterior/posterior), TR=53 ms, 12 TEs evenly spaced between 3.8 ms to 48.9 ms, bandwidth=365 Hz/voxel, axial plane field of view=24 cm, slice thickness=0.7 mm, acquisition matrix=342×342×150 reconstructed to 512×512×150. A partial phase encoding with a fraction of 0.70 and parallel imaging with reduction factor of 2 was used to shorten scan time. Deep brain nuclei, including dentate nuclei, red nuclei, substantia nigra, thalamus, globus pallidus, putamen, and caudate nuclei, are clearly differentiated from surrounding brain parenchyma as indicated by the illustrated arrows 1110 in FIG. 11. Additionally, white matter fiber tracts including optic radiation, genu and splenium of corpus callosum, internal and external capsules showed negative susceptibility relative to surrounding brain tissue as pointed by arrows 1115 in FIG. 11. A clear visualization of these brain structures provides useful brain anatomical information.

Visualizing Subthalamic Nuclei for Deep Brain Stimulation

Figure 12:
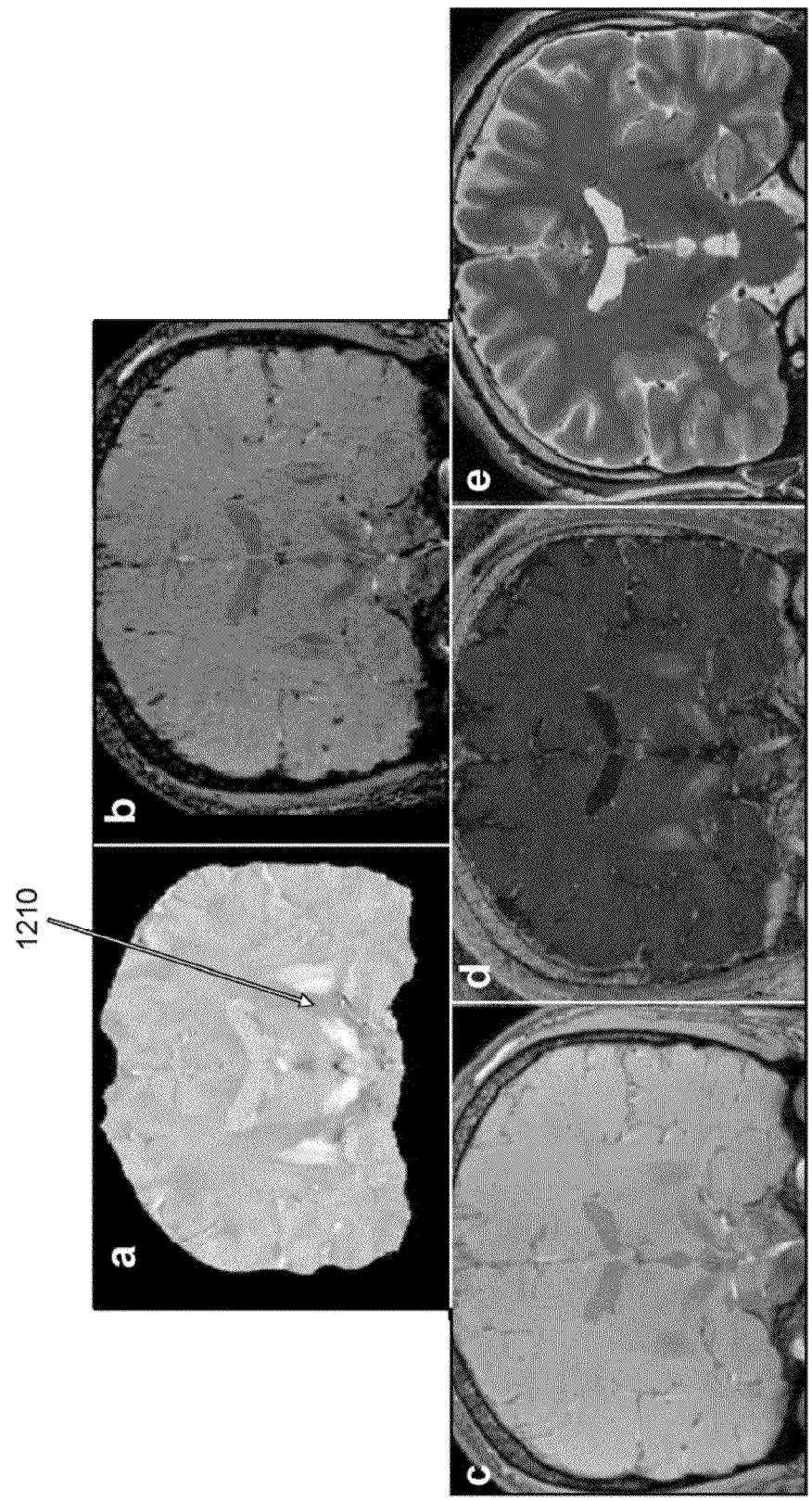
FIGS. 12a-12e are, in coronal view, an exemplary image of subthalamic nucleus on QSM, susceptibility-weighted image, magnitude image, R2* map and T2 weighted image, with QSM providing the best visual contrast between subthalamic nucleus (arrow) and surrounding tissue.

Among the brain nuclei, subthalamic nuclei can be of particular interest because it is a targeting site in deep brain stimulation. An improved visualization can be helpful for surgical planning when treating patients, e.g., patients with Parkinson's disease. An example is shown in FIG. 12. Among QSM (see FIG. 12a), susceptibility-weighted image (see FIG. 12b), magnitude image (see FIG. 12c), R2* map (see FIG. 12d) and T2 weighted image (see FIG. 12e), QSM can provide the best visual contrast between subthalamic nucleus 1210 and surrounding tissue. In this example, the complex MR data was acquired on a 3T scanner using a multi-echo gradient echo sequence with the following scanning parameters, flow compensated in readout direction (superior/inferior), TR=45 ms, 11 TEs evenly spaced between 4 ms to 40 ms, bandwidth=390 Hz/voxel, coronal plane field of view=24 cm, slice thickness=2 mm, acquisition matrix=320×320×40 reconstructed to 512×512×40. A partial phase encoding with a fraction of 0.70 and parallel imaging with reduction factor of 2 was used to shorten scan time, A T2 weighted image (T2WI) was also acquired for comparison. The imaging parameters were as follows for the T2WI, TE=86 ms, TR=8s, bandwidth=390 Hz/voxel, number of averaging=4. The scan time was under 5 minutes for both acquisitions. Among QSM, susceptibility weighted image, magnitude image, R2* map that can all be derived from the same multi-echo images and T2WI, QSM provides the best visualization of the subthalamic nuclei measured by the contrast-to-noise ratio, defined as the difference between peak voxel value of the subthalamic nuclei and neighboring background divided by the standard deviation of the signal intensity from a region of interest in the neighboring thalamic region.

Visualizing White Matter Lesions on Multiple Sclerosis Patients.

Figure 13:
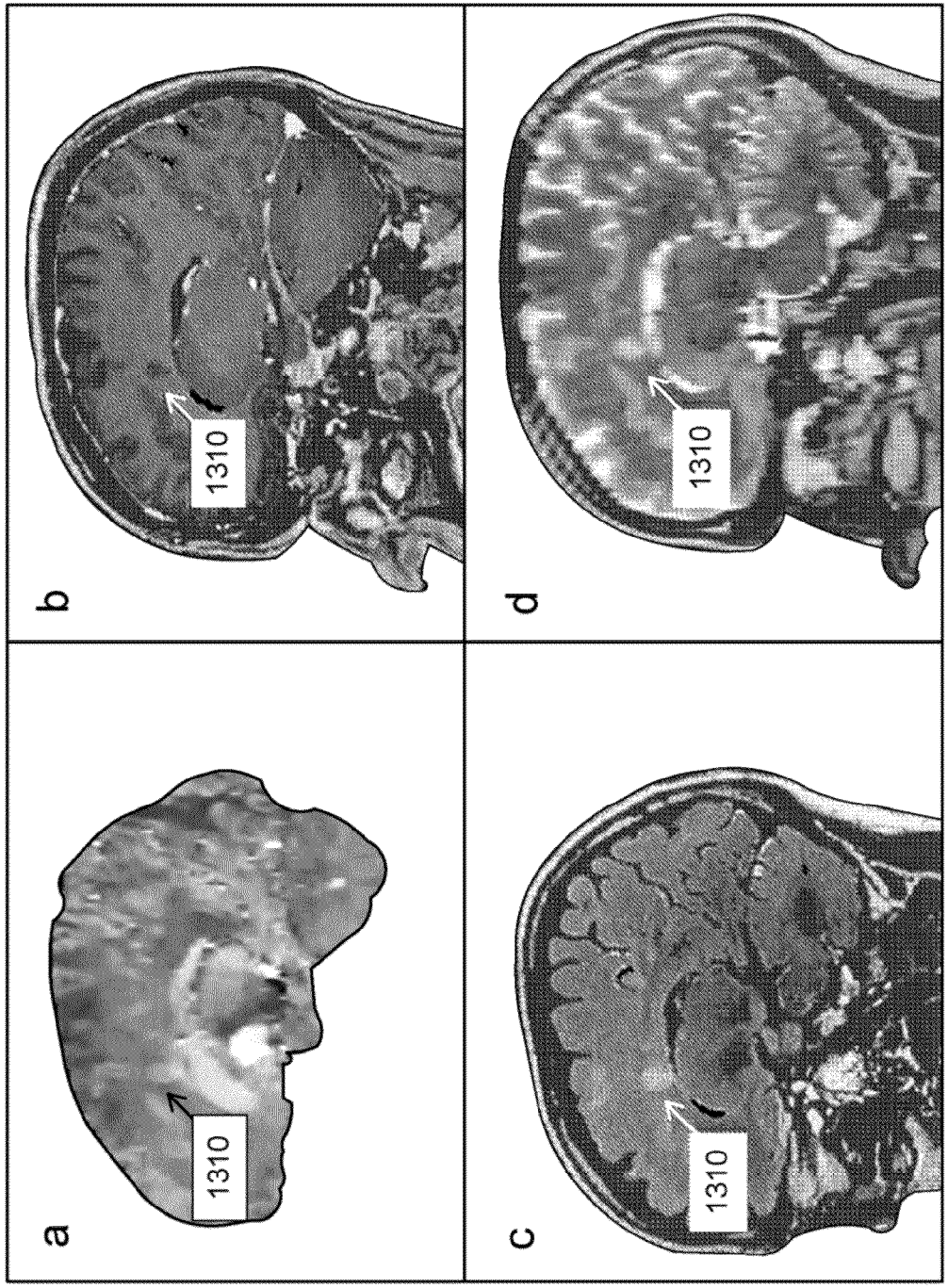
FIGS. 13a-13d are exemplary images of white matter lesions on QSM, T1 weighted image, T2 FLAIR image and T2 weighted image, providing an opportunity to stratify lesions and stage disease.

Quantitative susceptibility mapping can also provide additional information about white matter lesions commonly seen in patients with multiple sclerosis, as illustrated in FIG. 13. The lesions can have different appearances on QSM (see FIG. 13a), T1 weighted image (see FIG. 13b), T2 FLAIR image (see FIG. 13c) and T2 weighted image (see FIG. 13d), providing an opportunity to stratify lesions and stage disease. In this example, the complex MR data was acquired on a 3T scanner using a multi-echo gradient echo sequence with the following scanning parameters, flow compensated in readout direction (anterior/posterior), TR=57 ms, 11 TEs evenly spaced between 4.3 ms to 52.4 ms, bandwidth=300 Hz/voxel, axial plane field of view=24 cm, slice thickness=2 mm, acquisition matrix=416×320×60 reconstructed to 512×512×60. A partial phase encoding with a fraction of 0.70 and parallel imaging with reduction factor of 2 was used to shorten scan time. On the reconstructed QSM, Dawson finger can be recognized on QSM as hyperintense lesions through their morphology and the associated medullary veins 1310. Other hyperintense oval lesions can also be visualized, indicating iron deposition or demyelination. These additional information regarding the physical property of a lesion may provide complementary information to T1 weighted, T2 weighted and T2 FLAIR images for lesion stratification and disease staging.

Exemplary Cancer Imaging

Figure 14:
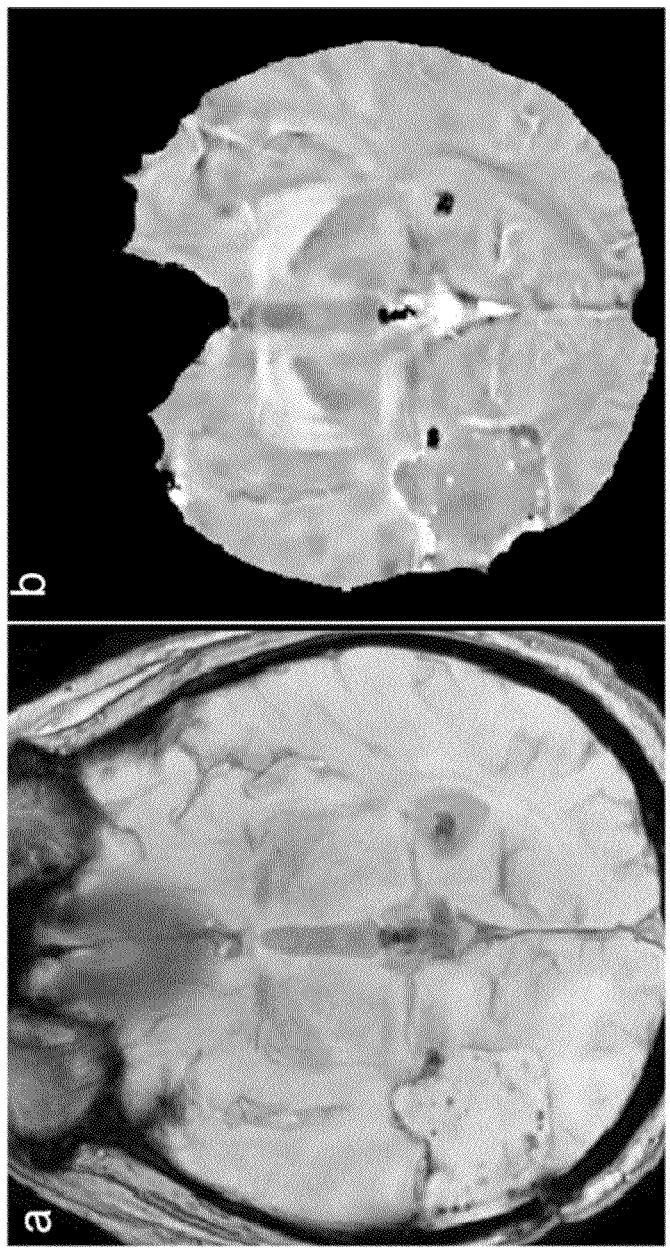
FIGS. 14a and 14b are exemplary images of brain tumor on magnitude image and QSM.

An exemplary quantitative susceptibility mapping can also be applied to image brain tumor, as illustrated in FIG. 14. This exemplary image was acquired on a 3T scanner using a multi-echo gradient echo sequence with the following scanning parameters, flow compensated in readout direction (anterior/posterior), TR=57 ms, 11 TEs evenly spaced between 4.3 ms to 52.4 ms, bandwidth=300 Hz/voxel, axial plane field of view=24 cm, slice thickness=2 mm, acquisition matrix=416×320×60 reconstructed to 512×512×46. A partial phase encoding with a fraction of 0.70 and parallel imaging with reduction factor of 3 was used to shorten scan time. The brain tumors demonstrated a range of susceptibility from diamagnetism to paramagnetism.

Contrast Agents Mapping

It has been shown in phantom and ex vivo that contrast agents, such as Gadolinium (Gd) or super-paramagnetic iron oxide (SPIO) nanoparticles, are paramagnetic and their susceptibility values linearly relate to their concentration through molar susceptibility, Therefore, quantitative susceptibility mapping provides a means to quantify contrast agents in vivo.

Figure 15:
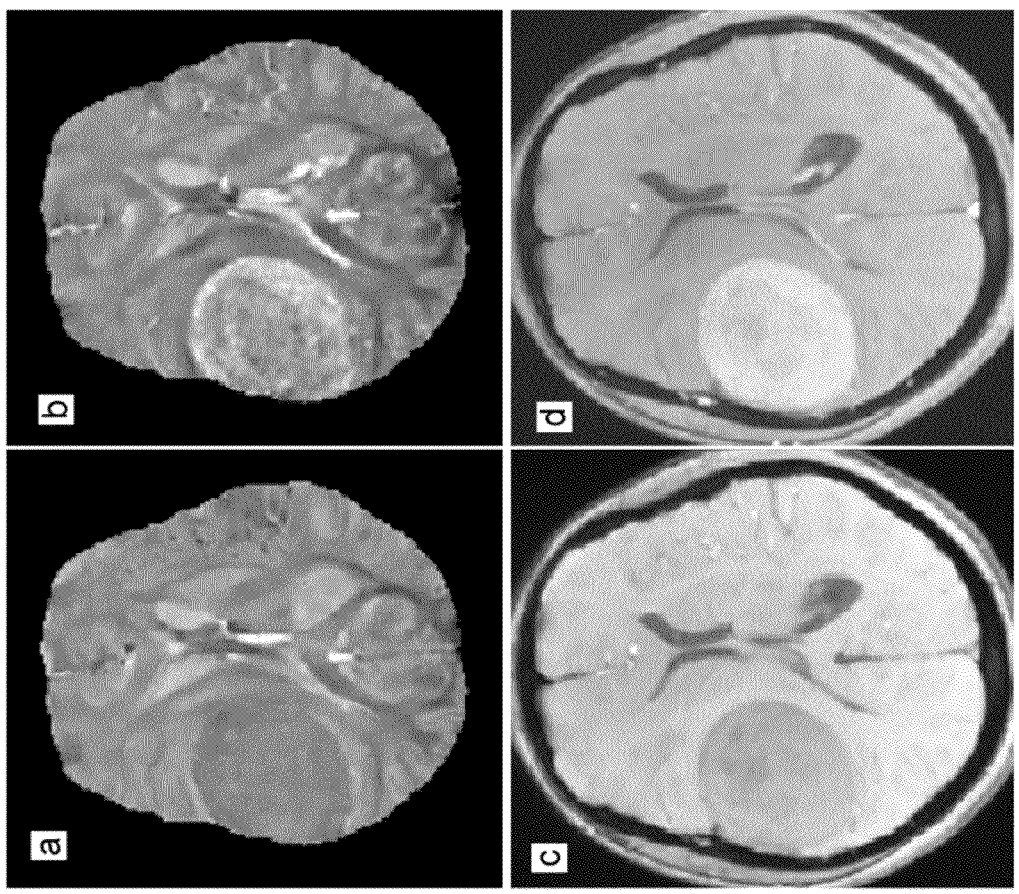
FIGS. 15a-15d are exemplary images of mapping contrast agents in brain tumor on QSM (top) and T1 weighted magnitude image (bottom)

In one example (e.g., as illustrated in FIG. 15), a brain tumor was imaged before and after contrast agent injection. The exemplary imaging parameters are as follows: flow compensated in readout direction (anterior/posterior), TR=45 ms, 12 TEs evenly spaced between 3 ms to 36 ms, bandwidth=521 Hz/voxel, axial plane field of view=24 cm, slice thickness=3 mm, acquisition matrix=240×240×52 reconstructed to 256×256×52. A parallel imaging with reduction factor of 2 was used to shorten scan time. Comparing the pre and post injection images, QSM showed that the enhancement was preferentially higher in the periphery (FIGS. 15*a*&*b*), indicating peripheral hypervasculature of the tumor, while the magnitude image showed an almost uniform enhancement (FIGS. 15*c*&*d*), likely due to the saturation in the nonlinear relationship between gadolinium concentration and signal intensity. The gadolinium concentration measure by QSM is 0.22 mM at the periphery and 0.017 mM in the center.

Unambiguous Calcification Identification

Figure 16:
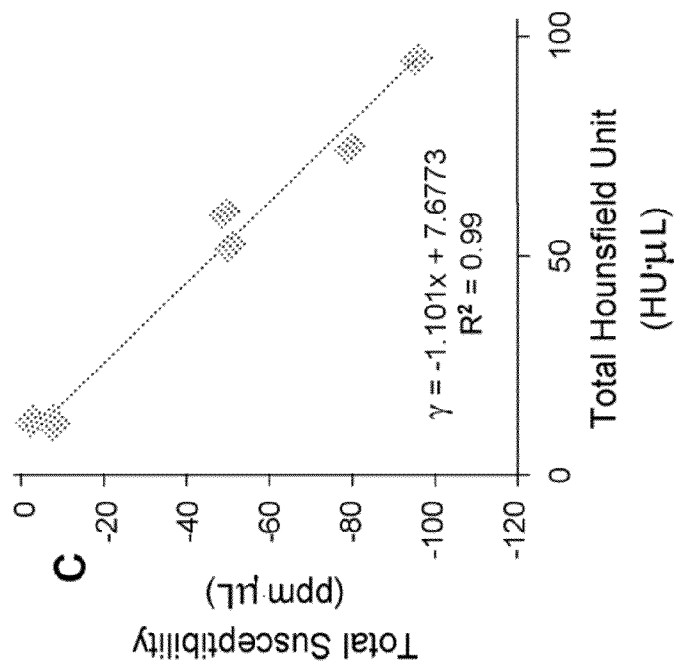
FIG. 16 are exemplary images of a calcified lesion on QSM, CT, and the correlation between QSM and CT.
Figure 16:
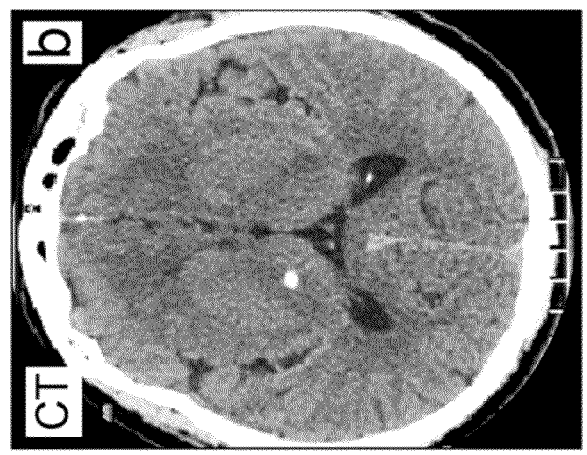
Figure 16:
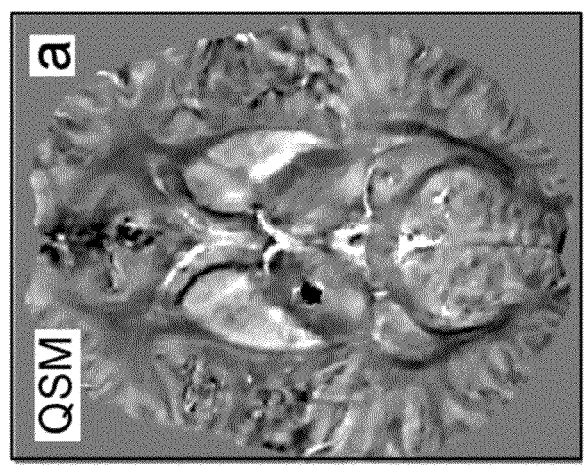

Quantitative susceptibility mapping can enable unambiguous calcification identification because calcification has a unique strong diamagnetic property among all known materials usually seen in human brains. A calcified lesion, which is hypointensity on QSM, can be easily identified and differentiated from other paramagnetic lesions such as a hemorrhage. An exemplary case is illustrated in FIG. 16. In this exemplary illustration, the complex MR data was acquired on a 3T scanner using a multi-echo gradient echo sequence with the following exemplary scanning parameters, flow compensated in readout direction (anterior/posterior), TR=53 ms, 8 TEs evenly spaced between 5 ms to 40 ms, bandwidth=365 Hz/voxel, axial plane field of view=24 cm, slice thickness=2 mm, acquisition inatrix=4416×320×70 reconstructed to 512×512×70. A parallel imaging with reduction factor of 2 was used to shorten scan time. An additional CT scan was also performed to confirm the presence of calcification as shown in FIG. 16*b*. If the total susceptibility of a calcified lesion is defined as the multiplication of voxel size with the sum of susceptibility values inside a manually segmented region of interest including the lesion, and the total Hounsfield unit is defined similarly on CT, there is an excellent correlation between total susceptibility and total Hounsfield unit in the calcified lesions as shown in FIG. 16*c*.

7. Visualization

Figure 17:
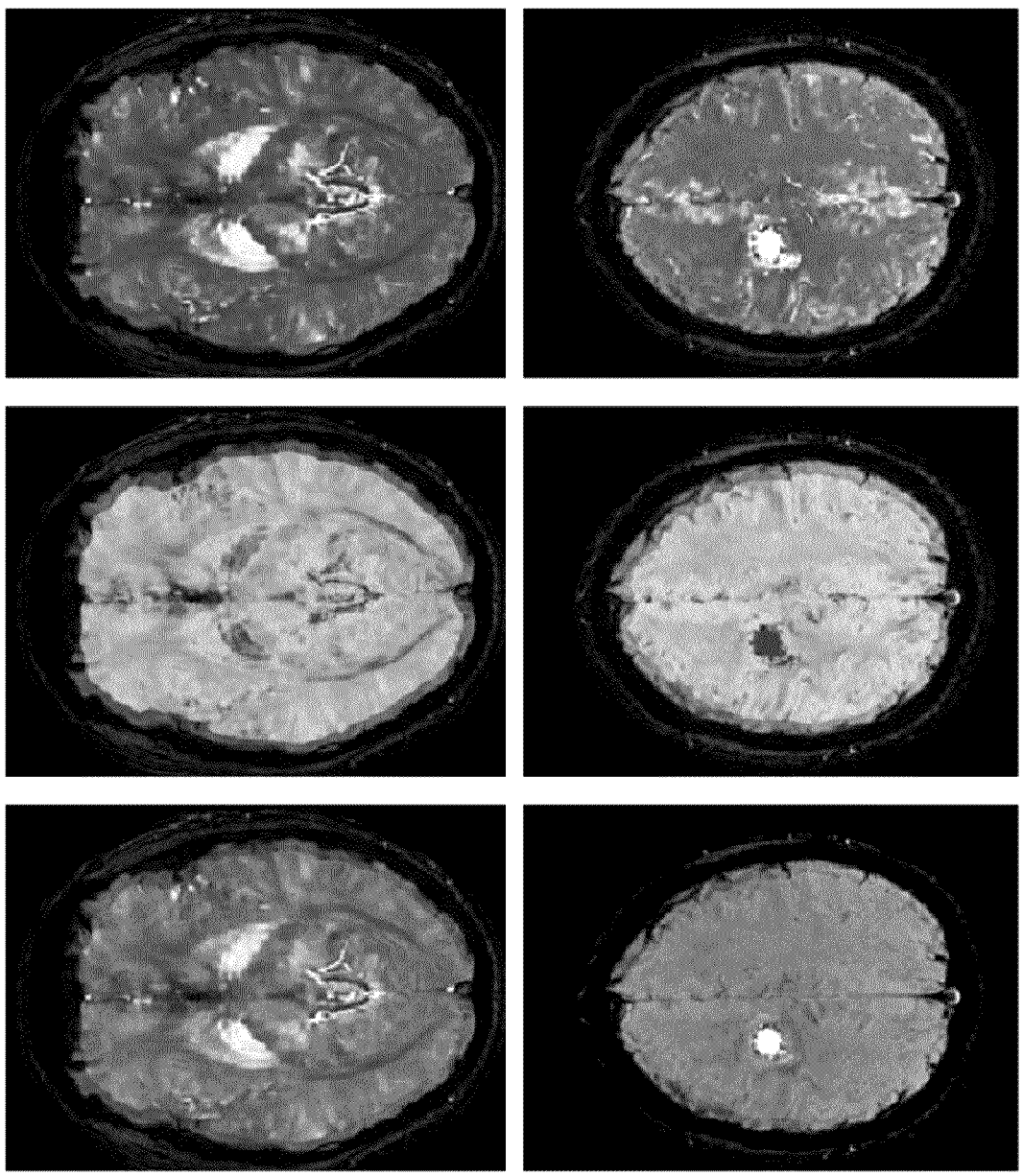
FIG. 17 are a set of exemplary images of fusing QSM onto anatomic images using gray and color schemes.

Since the QSM is a post-processing technique, the resultant images are naturally registered with the input images and can be fused onto the original images. When fusing with the original image in certain exemplary embodiments, the QSM image can be the foreground image and the magnitude image can be the background image. The transparency of the foreground image may vary from 0% to 100%, and may be color coded using various pseudo-color schemes. The display window and level of the background image can be adjusted independent of the foreground image, as illustrated in a set of exemplary images of FIG. 17. The volumetric QSM images can also be displayed in a 3 dimensional volume rendered view, a mean intensity projection view, a minimum intensity projection, or a maximum intensity projection view over several slices.

Additional Exemplary Embodiments

Figure 18:
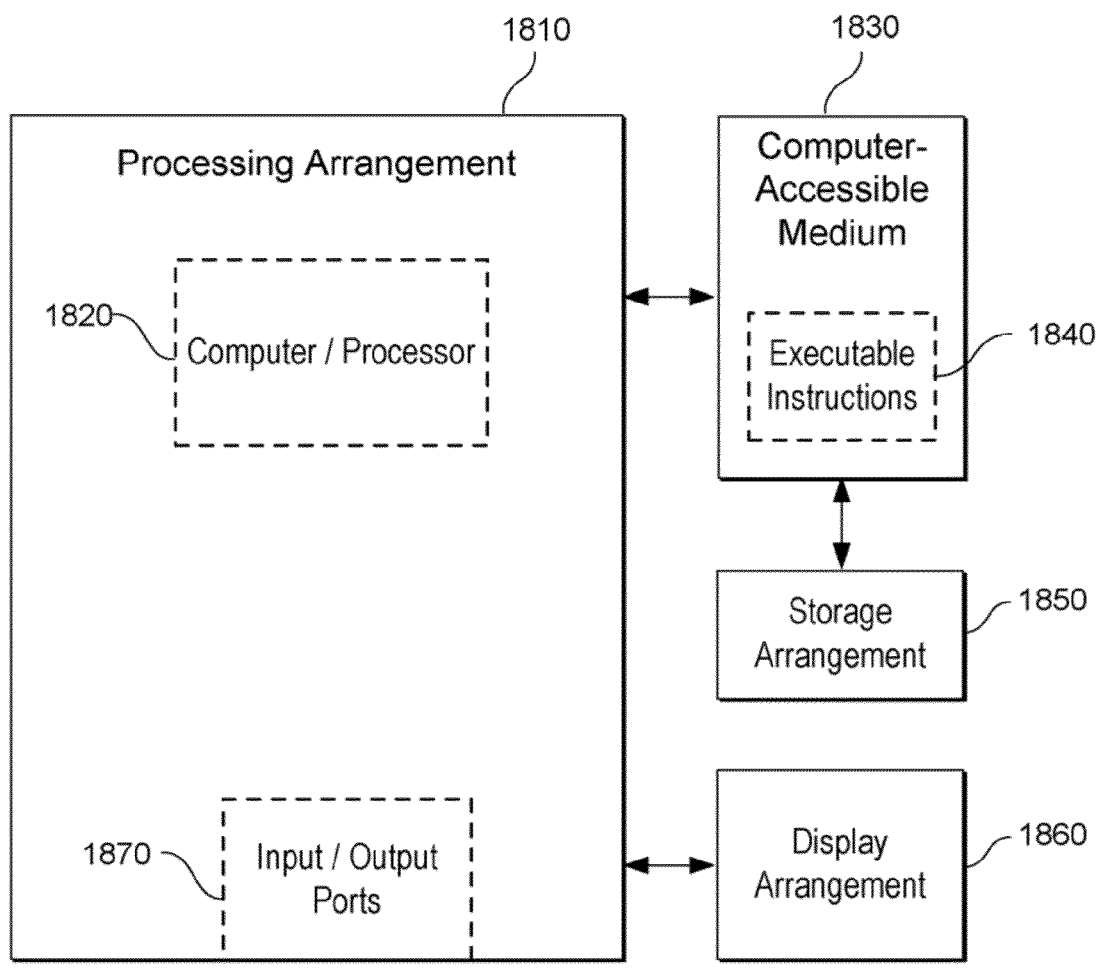
FIG. 18 is a block diagram of an exemplary embodiment of a system according to of the present disclosure.

FIG. 18 shows an exemplary block diagram of an exemplary embodiment of a system according to the present disclosure. For example, exemplary procedures in accordance with the present disclosure described herein can be performed by a processing arrangement and/or a computing arrangement 1810. Such processing/computing arrangement 1810 can be, e.g., entirely or a part of, or include, but not limited to, a computer/processor 1820 that can include, e.g., one or more microprocessors, and use instructions stored on a computer-accessible medium (e.g., RAM, ROM, hard drive, or other storage device).

As shown in FIG. 18, e.g., a computer-accessible medium 1830 (e.g., as described herein above, a storage device such as a hard disk, floppy disk, memory stick, CD-ROM, RAM, ROM, etc., or a collection thereof) can be provided (e.g., in communication with the processing arrangement 1810). The computer-accessible medium 1830 can contain executable instructions 1840 thereon. In addition or alternatively, a storage arrangement 1850 can be provided separately from the computer-accessible medium 1830, which can provide the instructions to the processing arrangement 1810 so as to configure the processing arrangement to execute certain exemplary procedures, processes and methods, as described herein above, for example.

Further, the exemplary processing arrangement 1810 can be provided with or include an input/output arrangement 1870, which can include, e.g., a wired network, a wireless network, the internet, an intranet, a data collection probe, a sensor, etc. As shown in FIG. 18, the exemplary processing arrangement 18 can be in communication with an exemplary display arrangement 1860, which, according to certain exemplary embodiments of the present disclosure, can be a touch-screen configured for inputting information to the processing arrangement in addition to outputting information from the processing arrangement, for example. Further, the exemplary display 1860 and/or a storage arrangement 1850 can be used to display and/or store data in a user-accessible format and/or user-readable format Indeed, the exemplary processing arrangement can be utilized to execute the exemplary procedures described herein, and according to the exemplary embodiments of the present disclosure.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. In addition, all publications and references referred to above can be incorporated herein by reference in their entireties. It should be understood that the exemplary procedures described herein can be stored on any computer accessible medium, including a hard drive, RAM, ROM, removable disks, CD-ROM, memory sticks, etc., and executed by a processing arrangement and/or computing arrangement which can be and/or include a hardware processors, microprocessor, mini, macro, mainframe, etc., including a plurality and/or combination thereof. In addition, certain terms used in the present disclosure, including the specification, drawings and claims thereof, can be used synonymously in certain instances, including, but not limited to, e.g., data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it can be explicitly being incorporated herein in its entirety. All publications referenced can be incorporated herein by reference in their entireties.

EXEMPLARY REFERENCES OF THE DISCLOSURE

1. Li, W., Wu, B., Liu, C., 2011. Quantitative susceptibility mapping of human brain reflects spatial variation in tissue composition. Neuroimage 55, 1645-1656.
2. Liu, C., 2010. Susceptibility tensor imaging. Magn Reson Med 63, 1471-1477.
3. Wu, B., Li, W., Guidon, A., Liu, C., 2012. Whole brain susceptibility mapping using compressed sensing. Magn Reson Med 67, 137-147.
4. Shmueli, K., de Zwart, J. A., van Gelderen, P., Li, T. Q., Dodd, S. J., Duyn, J. H., 2009. Magnetic susceptibility mapping of brain tissue in vivo using MRI phase data. Magn Reson Med 62, 1510-1522.
5. Haacke, E. M., Tang, J., Neelavalli, J., Cheng, Y. C., 2010. Susceptibility mapping as a means to visualize veins and quantify oxygen saturation. J Magn Reson Imaging 32, 663-676.
6. Liu, T., Liu, J., de Rochefort, L., Spincemaille, P., Khalidov, I., Ledoux, J. R., Wang, Y., 2011. Morphology enabled dipole inversion (MEDI) from a single-angle acquisition: comparison with COSMOS in human brain imaging. Magn Reson Med 66, 777-783.
7. Liu, T., Spincemaille, P., de Rochefort, L., Kressler, B., Wang, Y., 2009. Calculation of susceptibility through multiple orientation sampling (COSMOS): a method for conditioning the inverse problem from measured magnetic field map to susceptibility source image in MRI. Magn Reson Med 61, 196-204.
8. Schweser, F., Deistung, A., Lehr, B. W., Reichenbach, J. R., 2011. Quantitative imaging of intrinsic magnetic tissue properties using MRI signal phase: an approach to in vivo brain iron metabolism? Neuroimage 54, 2789-2807.
9. Wharton, S., Schafer, A., Bowtell, R., 2010. Susceptibility mapping in the human brain using threshold-based k-space division. Magn Reson Med 63, 1292-1304.
10. Wharton, S., Bowtell, R., 2010. Whole-brain susceptibility mapping at high field: a comparison of multiple- and single-orientation methods. Neuroimage 53, 515-525.
11. de Rochefort, L., Brown, R., Prince, M. R., Wang, Y., 2008. Quantitative MR susceptibility mapping using piece-wise constant regularized inversion of the magnetic field. Magn Reson Med 60, 1003-1009.
12. de Rochefort, L., Nguyen, T., Brown, R., Spincemaille, P., Choi, G., Weinsaft, J., Prince, M. R., Wang, Y., 2008. In vivo quantification of contrast agent concentration using the induced magnetic field for time-resolved arterial input function measurement with MRI. Med Phys 35, 5328-5339.
13. Liu, T., Spincemaille, P., de Rochefort, L., Wong, R., Prince, M., Wang, Y., 2010. Unambiguous identification of superparamagnetic iron oxide particles through quantitative susceptibility mapping of the nonlinear response to magnetic fields. Magn Reson Imaging 28, 1383-1389.
14. Li, L., 2001. Magnetic susceptibility quantification for arbitrarily shaped objects in inhomogeneous fields. Magn Reson Med 46, 907-916.
15. Li, L., Leigh, J. S., 2004. Quantifying arbitrary magnetic susceptibility distributions with MR. Magnetic Resonance in Medicine 51, 1077-1082.
16. Li, L., 2002. Averaging of harmonic physical fields over an annular region enclosing field sources. American Journal of Physics 70, 1029-1033.
17. Li, L., Leigh, J. S., 2001. High-precision mapping of the magnetic field utilizing the harmonic function mean value property. J Magn Reson 148, 442-448.
18. Koch, K. M., Papademetris, X., Rothman, D. L., de Graaf, R. A., 2006. Rapid calculations of susceptibility-induced magnetostatic field perturbations for in vivo magnetic resonance. Phys Med Biol 51, 6381-6402.
19. Marques, J. P., Bowtell, R., 2005, Application of a fourier-based method for rapid calculation of field inhomogeneity due to spatial variation of magnetic susceptibility. Concepts in Magnetic Resonance Part B-Magnetic Resonance Engineering 25B, 65-78.
20. Salomir, R., De Senneville, B. D., Moonen, C. T. W., 2003. A fast calculation method for magnetic field inhomogeneity due to an arbitrary distribution of bulk susceptibility. Concepts in Magnetic Resonance Part B-Magnetic Resonance Engineering 19B, 26-34.
21. Park, S. C., Park, M. K., Kang, M. G., 2003. Super-resolution image reconstruction: a technical overview. IEEE Signal Processing Magazine 20, 16.
22. Farsiu, S., Robinson, M. D., Elad, M., Milanfar, P., 2004. Fast and robust multiframe super resolution. IEEE transactions on image processing: a publication of the IEEE Signal Processing Society 13, 1327-1344.
23. Gudbjartsson, H., Patz, S., 1995. The Rician distribution of noisy MRI data. Magn Reson Med 34, 910-914.
24. Elad, M., Feuer, A., 1997. Restoration of a single super-resolution image from several blurred, noisy, and undersampled measured images. IEEE transactions on image processing: a publication of the IEEE Signal Processing Society 6, 1646-1658.
25. Gindi, G., Lee, M., Rangarajan, A., Zubal, I. G., 1993. Bayesian reconstruction of functional images using anatomical information as priors. Ieee Transactions on Medical Imaging 12, 670-680.
26. Baillet, S., Garnero, L., 1997. A Bayesian approach to introducing anatomo-functional priors in the EEG/MEG inverse problem. IEEE transactions on biomedical engineering 44, 374-385.
27. Kressler, B., de Rochefort, L., Liu, T., Spincemaille, P., Jiang, Q., Wang, Y., 2010. Nonlinear regularization for per voxel estimation of magnetic susceptibility distributions from MRI field maps. Ieee Transactions on Medical Imaging 29, 273-281.
28. Liu, J., Liu, T., de Rochefort, L., Ledoux, J., Khalidov, I., Chen, W., Tsiouris, A. J., Wisnieff, C., Spincemaille, P., Prince, M. R., Wang, Y., 2012. Morphology enabled dipole inversion for quantitative susceptibility mapping using structural consistency between the magnitude image and the susceptibility map. Neuroimage 59, 2560-2568.
29. Goldstein, R. M., Zebker, H. A., Werner, C. L., 1988. Satellite Radar Interferometry—Two-Dimensional Phase Unwrapping. Radio Science 23, 713-720.
30. de Rochefort, L., Liu, T., Kressler, B., Liu, J., Spincemaille, P., Lebon, V., Wu, J., Wang, Y., 2010. Quantitative susceptibility map reconstruction from MR phase data using bayesian regularization: validation and application to brain imaging. Magn Reson Med 63, 194-206.
31. Kressler, B., de Rochefort, L., Liu, T., Spincemaille, P., Jiang, Q., Wang, Y., 2010. Nonlinear regularization for per voxel estimation of magnetic susceptibility distributions from MRI field maps. IEEE Trans Med Imaging 29, 273-281.
32. Liu, J., Liu, T., de Rochefort, L., Ledoux, J., Khalidov, I., Chen, W., Tsiouris, A. J., Wisnieff, C., Spincemaille, P., Prince, M. R., Wang, Y., 2012. Morphology enabled dipole inversion for quantitative susceptibility mapping using structural consistency between the magnitude image and the susceptibility map. Neuroimage.
33. Rudin, L. I., Osher, S., Fatemi, E., 1992. Nonlinear Total Variation Based Noise Removal Algorithms. Physica D 60, 259-268.
34. Liu, T., Khalidov, I., de Rochefort, L., Spincemaille, P., Liu, J., Tsiouris, A. J., Wang, Y., 2011. A novel background field removal method for MRI using projection onto dipole fields (PDF). NMR Biomed 24, 1129-1136.
35. Smith, S. M., 2002. Fast robust automated brain extraction. Hum Brain Mapp 17, 143-155.
36. Zubal, I. G., Harrell, C. R., Smith, E. O., Rattner, Z., Gindi, G., Hoffer, P. B., 1994. Computerized three-dimensional segmented human anatomy. Med Phys 21, 299-302.
37. Broderick, J., Connolly, S., Feldmann, E., Hanley, D., Kase, C., Krieger, D., Mayberg, M., Morgenstern, L., Ogilvy, C. S., Vespa, P., Zuccarello, M., 2007. Guidelines for the management of spontaneous intracerebral hemorrhage in adults: 2007 update: a guideline from the American Heart Association/American Stroke Association Stroke Council, High Blood Pressure Research Council, and the Quality of Care and Outcomes in Research Interdisciplinary Working Group. Circulation 116, e391-413.
38. Flaherty, M. L., Haverbusch, M., Sekar, P., Kissela, B., Kleindorfer, D., Moomaw, Sauerbeck, L., Schneider, A., Broderick, J. P., Woo, D., 2006. Long-term mortality after intracerebral hemorrhage. Neurology 66, 1182-1186.
39. Kidwell, C. S., Chalela, J. A., Saver, J. L., Starkman, S., Hill, M. D., Demchuk, A. M., Butman, J. A., Patronas, N., Alger, J. R., Latour, Li., Lu by, M. L., Baird, A. E., Leary, M. C., Tremwei, M., Ovbiagele, B., Fredieu, A., Suzuki, S., Villablanca, J. P., Davis, S., Dunn, B., Todd, J. W., Ezzeddine, M. A., Haymore, Lynch, J. K. Davis, L., Warach, S., 2004. Comparison of MRI and CT for detection of acute intracerebral hemorrhage. JAMA 292, 1823-1830.
40. Christoforidis, G. A., Slivka, A., Mohammad, Y., Karakasis, C., Avutu, B., Yang, M., 2007. Size matters: hemorrhage volume as an objective measure to define significant intracranial hemorrhage associated with thrombolysis. Stroke 38, 1799-1804.
41. Schabel, M. C., Parker, D. L., 2008. Uncertainty and bias in contrast concentration measurements using spoiled gradient echo pulse sequences. Phys Med Biol 53, 2345-2373.
42. Chen, Z., Johnston, L. A., Kwon, D. H., Oh, S. H., Cho, Z. H., Egan, G. F., 2010. An optimised framework for reconstructing and processing MR phase images. Neuroimage 49, 1289-1300,
43. Robinson, S., Grabner, G., Witoszynskyj, S., Trattnig, S., 2011, Combining phase images from multi-channel RF coils using 3D phase offset maps derived from a dual-echo scan. Magri Reson Med 65, 1638-1648.
44. Ghiglia, D. C., Pritt, M. D., 1998. Two-dimensional phase unwrapping: theory, algorithms, and software. Wiley, New York.
45. Schofield, M. A., Zhu, Y. M., 2003. Fast phase unwrapping algorithm for interferometric applications. Optics Letters 28, 1194-1196.
46. Björck, Å., 1996. Numerical methods for least squares problems. SIAM, Philadelphia.
47. Reeder, S. B., Pineda, A. R., Wen, Z., Shimakawa, A., Yu, H., Brittain, J. H., Gold, G. E., Beaulieu, C. H., Pelc, N. J., 2005. Iterative decomposition of water and fat with echo asymmetry and least-squares estimation (IDEAL): application with fast spin-echo imaging. Magn Reson Med 54, 636-644.
48. Hernando, D., Kellman, P., Haldar, J. P., Liang, Z. P., 2010. Robust water/fat separation in the presence of large field inhomogeneities using a graph cut algorithm. Magn Reson Med 63, 79-90.

What is claimed is:
1. A system for generating one or more images of an object, the system comprising:
a processor;
a graphical output module communicatively coupled to the processor;
a input module communicatively coupled to the processor;
a non-transitory computer storage medium encoded with a computer program, the program comprising instructions that when executed by processor cause the processor to perform operations comprising:
receiving, by the input module, magnetic resonance imaging (MRI) data obtained by a magnetic resonance scanner, wherein the MRI data is complex and comprises:
magnitude and phase information or real and imaginary information regarding the object, and
Gaussian noise;
determining a magnetic field based on the MRI data, the magnetic field comprising a background magnetic field component and a local magnetic field component, the background magnetic field component corresponding to a portion of the magnetic field induced by magnetic sources outside a region of interest of the object, and the local magnetic field component corresponding to a portion of the magnetic field induced by magnetic sources inside the region of interest of the object;

determining the background magnetic field component based on the MRI data;

removing the background magnetic field component from the magnetic field to obtain the local magnetic field component;

estimating a magnetic susceptibility distribution of the object based on the local magnetic field component, wherein estimating the magnetic susceptibility distribution of the subject comprises:

determining a cost function, the cost function relating at least a data fidelity term associated with a likelihood function associated with the Gaussian noise and a regularization term associated with prior information regarding the magnetic susceptibility distribution, wherein the data fidelity term is expressed as one or more complex exponential functions of the local field component and the magnetic susceptibility distribution; and determining an estimated magnetic susceptibility distribution based on the cost function; and presenting, on a display device communicatively coupled to the graphical output module, one or more images of the object generated based on the estimated susceptibility distribution of the object.

2. The system of claim 1, wherein the background magnetic field component is determined by utilizing a Laplace operator.

3. The system of claim 1, wherein the prior information regarding the magnetic susceptibility distribution is determined based on an L1 norm and structural information of the object estimated from acquired images of the object.

4. The system of claim 1, wherein the object comprises a subthalamic nucleus of a brain, and wherein generating one or more images of the object comprises generating one or more images depicting the subthalamic nucleus.

5. The system of claim 1, wherein the object comprises at least one of a multiple sclerosis lesion, a cancerous lesion, a calcified lesion, or a hemorrhage, wherein generating one or more images of the object comprises generating one or more images depicting at least one of the multiple sclerosis lesion, the cancerous lesion, the calcified lesion, or the hemorrhage.

6. The system of claim 1, the operations further comprising:

quantifying, based on the one or more images, a distribution of contrast agents introduced into the object in the course of a contrast enhanced magnetic resonance imaging procedure.

7. The system of claim 1, wherein determining the estimated magnetic susceptibility distribution comprises minimizing the cost function.

8. A method for generating one or more images of an object, the method comprising:

receiving magnetic resonance imaging (MRI) data obtained by a magnetic resonance scanner, wherein the MRI data is complex and comprises:

magnitude and phase information or real and imaginary information regarding the object, and Gaussian noise;

determining a magnetic field based on the MRI data, the magnetic field comprising a background magnetic field component and a local magnetic field component, the background magnetic field component corresponding to a portion of the magnetic field induced by magnetic sources outside a region of interest of the object, and the local magnetic field component corresponding to a portion of the magnetic field induced by magnetic sources inside the region of interest of the object;

determining the background magnetic field component based on the MRI data;

removing the background magnetic field component from the magnetic field to obtain the local magnetic field component;

estimating a magnetic susceptibility distribution of the object based on the local magnetic field component, wherein estimating the magnetic susceptibility distribution of the subject comprises:

determining a cost function, the cost function relating at least a data fidelity term associated with a likelihood function associated with the Gaussian noise and a regularization term associated with prior information regarding the magnetic susceptibility distribution, wherein the data fidelity term is expressed as one or more complex exponential functions of the local field component and the magnetic susceptibility distribution; and determining an estimated magnetic susceptibility distribution based on the cost function; and presenting, on a display device, one or more images of the object generated based on the estimated susceptibility distribution of the object.

9. The method of claim 8, wherein the background magnetic field component is determined by utilizing a Laplace operator.

10. The method of claim 8, wherein the prior information regarding the magnetic susceptibility distribution is determined based on an L1 norm and structural information of the object estimated from acquired images of the object.

11. The method of claim 8, wherein the object comprises a subthalamic nucleus of a brain, and wherein generating one or more images of the object comprises generating one or more images depicting the subthalamic nucleus.

12. The method of claim 8, wherein the object comprises at least one of a multiple sclerosis lesion, a cancerous lesion, a calcified lesion, or a hemorrhage, wherein generating one or more images of the object comprises generating one or more images depicting at least one of the multiple sclerosis lesion, the cancerous lesion, the calcified lesion, or the hemorrhage.

13. The method of claim 8, the operations further comprising:

quantifying, based on the one or more images, a distribution of contrast agents introduced into the object in the course of a contrast enhanced magnetic resonance imaging procedure.

14. The method of claim 8, wherein determining the estimated magnetic susceptibility distribution comprises minimizing the cost function.

* * * * *